(12) United States Patent
Beug et al.

(10) Patent No.: US 6,830,923 B1
(45) Date of Patent: Dec. 14, 2004

(54) GENETICS UNITS FOR INHIBITING THE FUNCTION OF RNA

(75) Inventors: Hartmut Beug, Vienna (AT); Max L. Birnstiel, Vienna (AT); Matthew Cotten, Vienna (AT); Ernst Wagner, Langenzersdorf (AT); Harald Kandolf, Vienna (AT)

(73) Assignee: Boehringer Inglheim International GmbH, Ingelheim am Rhein (DE)

( * ) Notice: Subject to any disclaimer, the term of this patent is extended or adjusted under 35 U.S.C. 154(b) by 0 days.

(21) Appl. No.: 07/947,982

(22) Filed: Sep. 21, 1992

Related U.S. Application Data

(63) Continuation of application No. 07/494,184, filed on Mar. 15, 1990, now abandoned.

(30) Foreign Application Priority Data

Mar. 16, 1989 (AT) ............................................. A 609/89

(51) Int. Cl.[7] ........................ C12N 15/00; C12N 15/09; C12N 15/63; C07H 21/04; C07H 21/02
(52) U.S. Cl. ................... 435/320.1; 536/23.1; 536/24.5
(58) Field of Search .......................... 435/320.1, 172.1, 435/172.9, 91, 172.3; 536/24.5, 23.1, 27, 23.2; 514/44

(56) References Cited

U.S. PATENT DOCUMENTS

| | | | |
|---|---|---|---|
| 4,740,463 A | * 4/1988 | Weinberg et al. | ............. 435/91 |
| 4,902,505 A | * 2/1990 | Pardridge et al. | ........... 530/350 |
| 5,354,844 A | * 10/1994 | Beug et al. | |
| 5,792,645 A | * 8/1998 | Beug et al. | |

OTHER PUBLICATIONS

Uhlenbeck (1987), Nature, vol. 328, pp 596–600.*
Haseloff et al. (1988), Nature, vol. 324, pp 585–591.*
Wu et al. (1987), Journal of Biol. Chem, vol 262, pp 4429–4432.*
Wu et al. (1988), Journal of Biol Chem, vol. 263, pp 14621–14624.*
Jennings et al. (1987), Embo J., vol 6, pp 3043–3047.*
Hofstetter et al. (1981), Cell, vol 24, pp 573–585.*
Simons et al. (1988), Gene, vol. 72, pp 35–44.*
Branch A good antisense molecule is hard to find TIBS vol. 23 pp. 45–50.*

* cited by examiner

*Primary Examiner*—James Ketter
*Assistant Examiner*—Konstantina Katcheves
(74) *Attorney, Agent, or Firm*—Sterne, Kessler, Goldstein & Fox PLLC

(57) ABSTRACT

The invention relates to a genetic unit, optionally present as a multiple-copy, for inhibiting RNA. The unit contains the transcription units necessary for transcription by polymerase III and a DNA coding for inhibiting RNA, which is arranged within the unit in such a way that the transcribed RNA is part of the polymerase III transcript. Using these units it is possible to achieve increased stability of the inhibiting RNA, which may occur in the form of ribozymes or antisense-RNAs, whilst maintaining an undiminished activity.

The invention further relates to a process for introducing the genetic units into the cell, the use of these units and pharmaceutical preparations containing them.

27 Claims, 15 Drawing Sheets

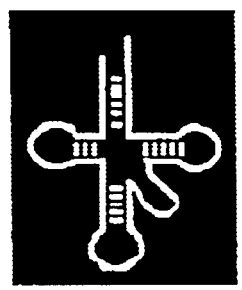
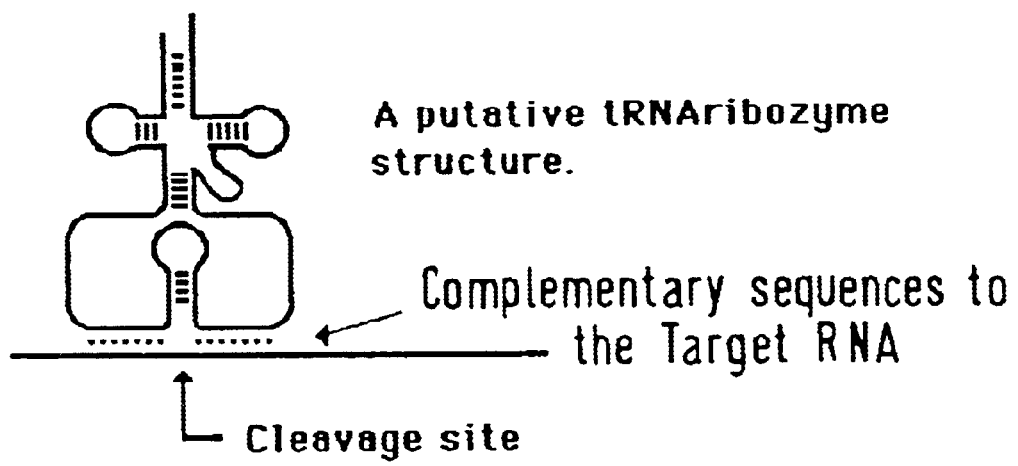
The compact structure of a tRNA molecule
A putative tRNAribozyme structure.
Complementary sequences to the Target RNA
Cleavage site
FIG. 1.

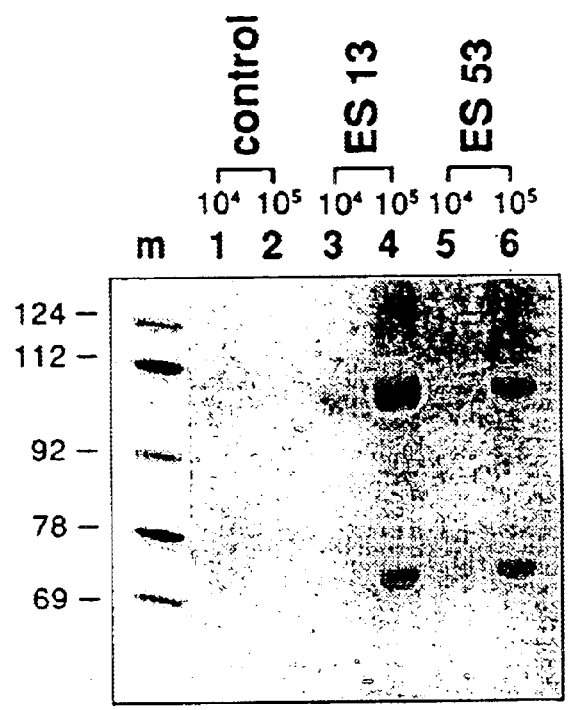
FIG. 8.
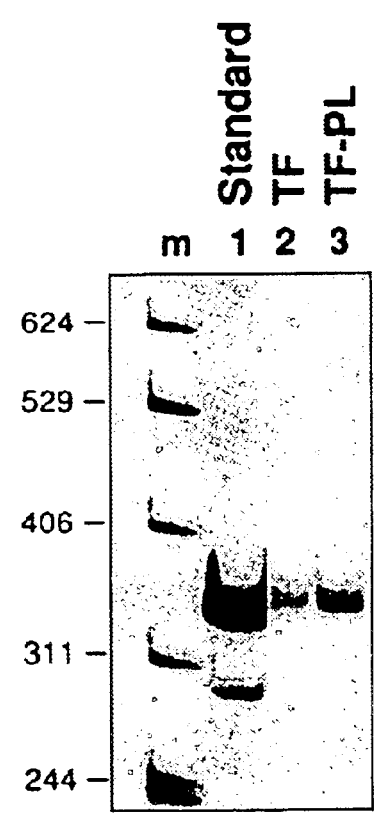
FIG. 9.
FIG. 10.
A
B
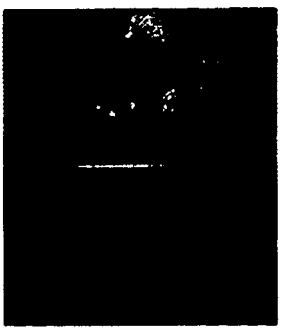
C tRNAmet
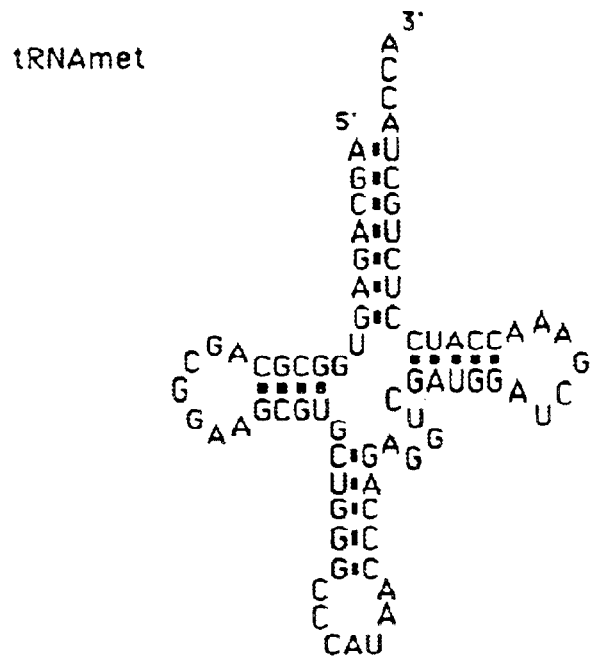
FIG. 11.
tRNArib T: truncated
anticodon stem
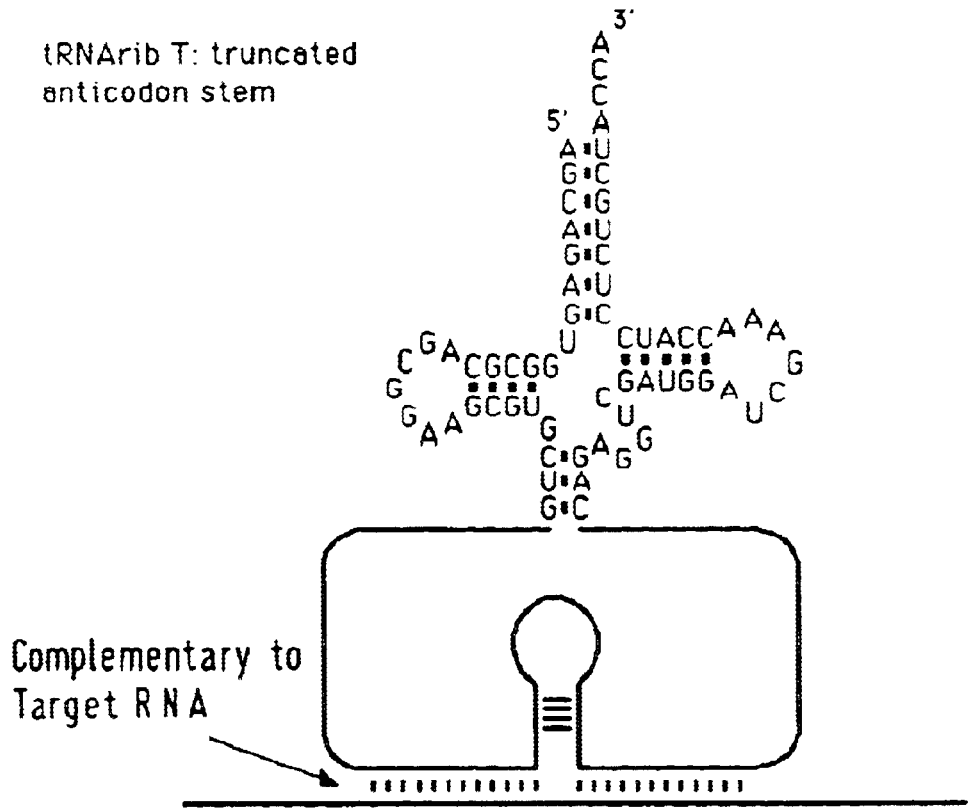
Complementary to
Target RNA

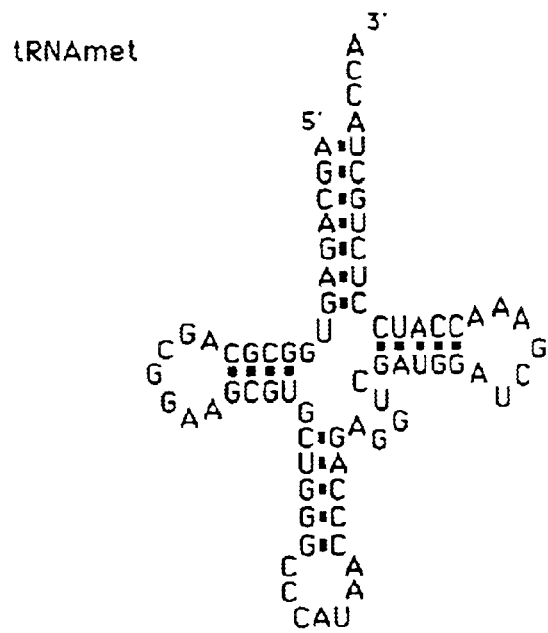
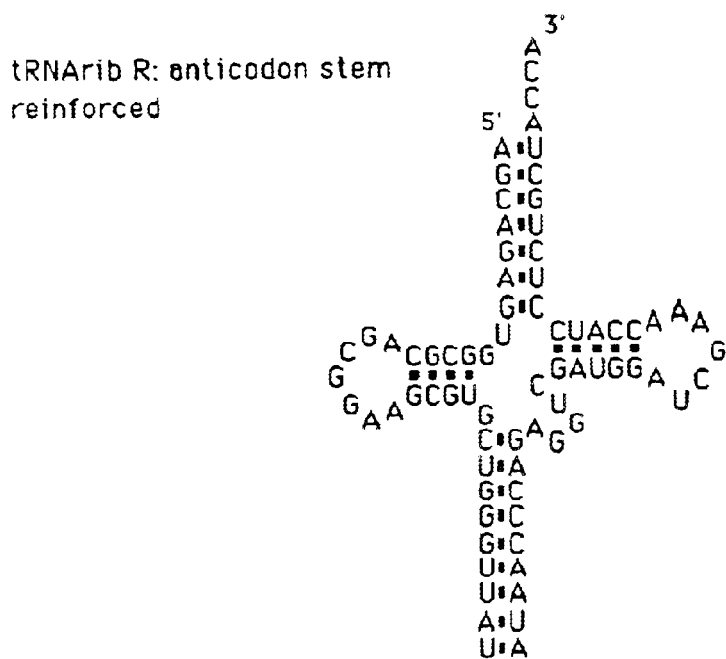
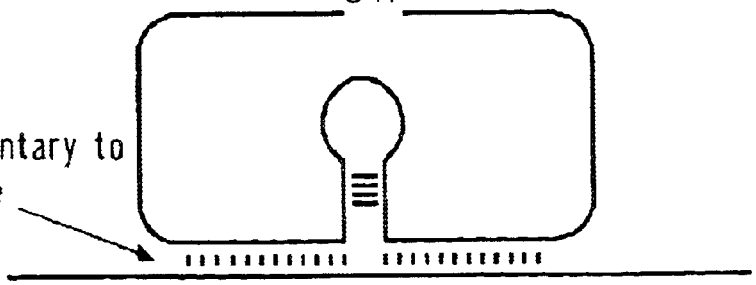
FIG. 12.

Lane 1: Molecular weight markers
Lane 2: RibtRNA T (truncated anticodon stem) +
    tRNAmet (Inj.conc.10:1)
Lane 3: RibtRNA R (reinforced anticodon stem) +
    tRNAmet (Inj.conc.10:1)

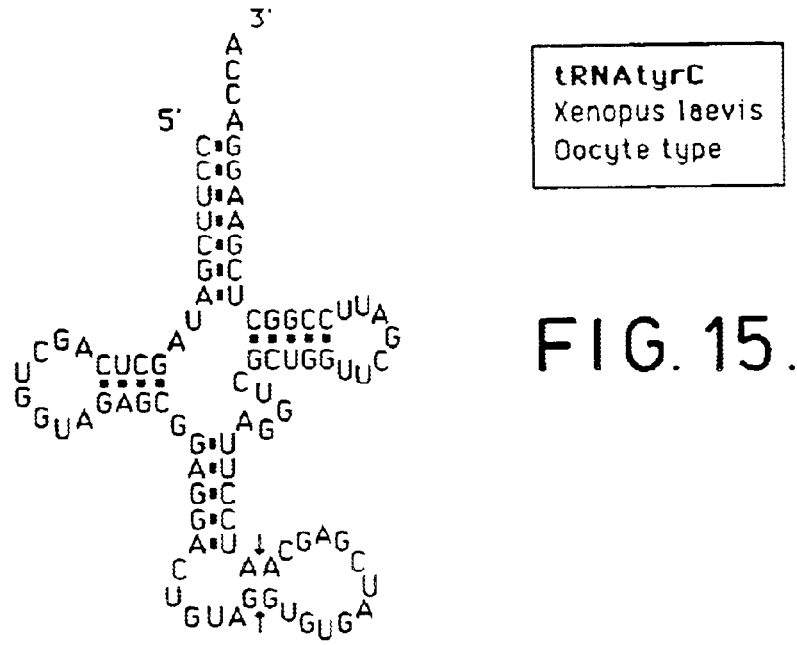
FIG. 15.
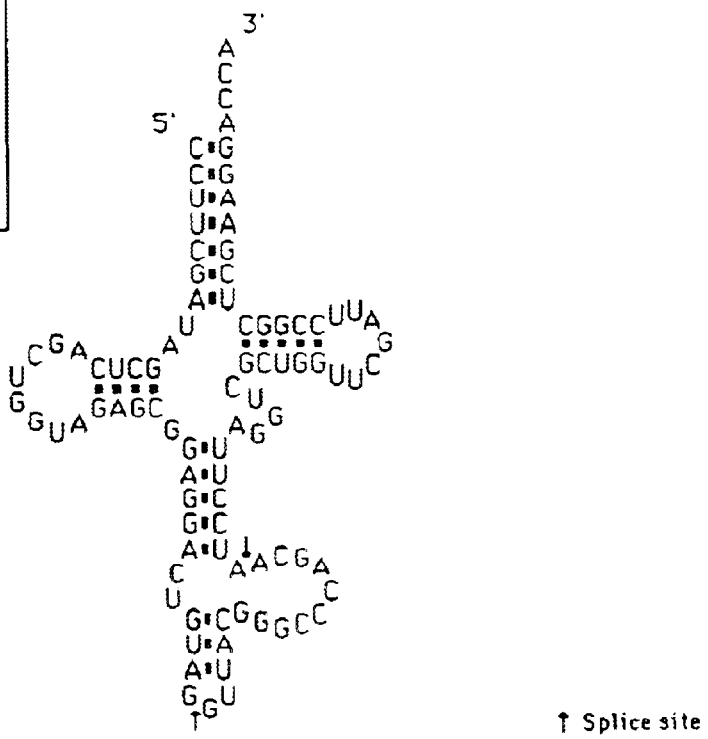
† Splice site

Lane 1: Molecular weight markers
Lane 2: tRNAtyrM + 5S RNA (Inj. conc. 50:1)
Lane 3  tRNAtyrC + 5S RNA (Inj. conc. 50:1)

Lanes 1 and 5: Molecular weight markers
Lane 2: Ribt RNA HP + 5S RNA (Inj. conc. 20:1)
Lane 3: Ribt RNA C + 5S RNA (Inj. conc. 1:1)
Lane 4: Ribt RNA D + 5S RNA (Inj. conc. 20:1)

GENETICS UNITS FOR INHIBITING THE FUNCTION OF RNA

This application is a continuation, of application Ser. No. 07/494,184, filed Mar. 15, 1990, now abandoned.

FIELD OF THE INVENTION

This invention relates to the specific inhibition of RNA by interaction with RNA.

BACKGROUND OF THE INVENTION

The specific inhibition of genes by oligonucleotides, e.g. in order to achieve a therapeutic blocking of deregulated oncogenes or viral genes, is based on the ability of such complementary RNA or DNA so-called antisense-oligonucleotides to hybridise with mRNAs, processing signals or pre-mRNAs and in this way interrupt the transfer of information from genes to proteins.

The use of antisense DNA results in the breakdown of complementary target RNA by RNAse H-cleaving of the hybrid formed, resulting in the irreversible destruction of the complementary RNA.

When antisense RNA is used, a so-called hybrid arrest of translation or processing occurs, the RNA/RNA hybrids constituting the structural obstacle. It is assumed that such hybrids accumulate in the cells; their subsequent fate has not hitherto been investigated. As far as is known at present, this mechanism is largely thought to be a reversible event. The use of antisense-RNA molecules has the advantage that these molecules may either be synthesized in vitro and introduced into the cells or that the genes coding for them can be introduced into the cells so that the inhibiting RNA can be produced within the cell. However, nobody has hitherto succeeded in bringing such genes into a form which makes it possible to produce an effective quantity of antisense RNA in the cell.

Very recently, a third principle of RNA inhibition has been discovered and made available for use in vitro.

This principle is based on the ability of RNA molecules the so-called ribozymes, to recognise certain RNA sequences, bind to them and cleave them. It was derived from the autocatalytic cleavage reactions of RNA molecules in plant viroids and satellite RNA observed in vivo.

On the basis of certain structural requirements for the ribozyme catalysed RNA cleavage, it is now possible to construct de novo ribozymes which have an endonuclease activity directed in trans to a certain target sequence. Since these ribozymes, of which the ones which have been most carefully researched are known as hammer-head ribozymes on account of their structure, can act on numerous different sequences, the corresponding ribozyme can be "made to measure" for virtually any RNA substrate. This makes ribozymes interesting and extremely flexible tools for inhibiting specific genes, with the result that they are a promising alternative to antisense constructs, which have already demonstrated potential therapeutic use.

One ribozyme model currently known which has so far been researched most thoroughly has three structural domains; on the basis of this model, ribozymes against CAT-mRNA have already been successfully constructed (Haseloff et al., 1988; Uhlenbeck et al., 1987):

The three domains comprise:

a) a highly conserved region of nucleotides flanking the cleavage site in the 5' direction. This usually means the sequence GUC, although modification in the GUA or GUU also showed a substantially undiminished cleaving activity. Cleaving was also found after the sequences CUC, and to a lesser extent for AUC and UUC as well (the requirements for efficient cleaving have not yet been fully explained).

b) the highly conserved sequences contained in naturally occurring cleavage domains of ribozymes, forming a sort of base-paired stem;

c) the regions which flank the cleavage site on both sides and ensure the exact arrangement of the ribozyme in relation to the cleavage site and the cohesion of the substrate and enzyme (in the experiments carried out hitherto, 8 bases were selected on each side).

RNA enzymes can be constructed according to this model and have already proved suitable in vitro for the efficient and specific cleaving of RNA sequences (Haseloff et al., 1988).

Very recently, further types of autocatalytic RNA cleavage activity were discovered which may be used for the targeted RNA inhibition. One of these models is the so-called hairpin ribozyme, the active site of which is derived from the minus strand of the satellite RNA of tobacco ring spot virus (Hampel and Tritz, 1989). Other self-cleaving RNA activities are associated with hepatitis delta virus (Kuo et al., 1988; Sharmeen et al., 1988; Wu et al., 1989) and with RNAseP (Altman et al., 1988).

The experiments which preceded the studies for the present invention served to compare the activities of antisense RNA, antisense DNA and ribozymes. These experiments were carried out using the snRNP U7-dependant histone-preRNA-processing reaction, in that an in vitro system which processes U7-dependent histone-preRNA (Mowry et al., 1987, Soldati et al., 1988). It was found that antisense RNA is the most potent inhibitor, and the inhibition is reversible. The inhibitory effects of antisense DNA and of ribozymes of the hammer-head type, both of which are irreversible, were within the same order of magnitude, each requiring an approximately one thousand-fold excess over the substrate RNA to achieve total inhibition.

Whereas the previous tests had been carried out with ribozymes with naked RNA in protein-free systems, the preliminary tests for the present invention were the first experiments to demonstrate that synthetically produced ribozymes directed to a specific sequence show a cleaving activity even in a medium which contains protein. This fact provided a first indication of a potential use in vivo.

One of the limiting factors in the use of ribozymes to inhibit the expression of specific genes would be in the build-up of a ribozyme concentration which is sufficient to efficiently rule out a specific biological reaction; the reasons for this would be, as in the use of antisense RNA, the inadequate stability of the RNA, among other things.

SUMMARY OF THE INVENTION

The aim of the present invention was to provide a system for using mRNA as an in vivo inhibitor of mRNA, which overcomes the previous restrictions in the use of RNA, by making an effective concentration of inhibition RNA available in the cell.

This aim is achieved according to the invention by means of a genetic unit which contains the transcription unit required for transcription by polymerase III and a DNA coding for the RNA which inhibits RNA function, this DNA being arranged within the genetic unit in such a way that the inhibiting RNA is part of the polymerase III transcript.

BRIEF DESCRIPTION OF THE FIGURES

FIG. 1. Diagrammatic representation of tRNA ribozyme.

Lane m: molecular weight marker pBR322, cleaved with HpaII and radioactively labelled using the Klenow fragment of DNA polymerase with alpha $^{32}$P CTP. The molecular weights of some of the fragments (in nucleotides) are shown on the left.

Lane 2: erbB-target mRNA (20,000 cpm, 20 fM) without incubation.

Lane 2: erbB-target mRNA (20,000 cpm, 20 fM) incubated with MgCl$_2$ at 37° without ribozymes.

Lane 3: erbB-target mRNA (20,000 cpm, 20 fM) incubated with ES13-RNA (1 fM).

Lane 4: erbB-target mRNA (20,000 cpm, 20 fM) incubated with ES53-RNA.

Figure 5:
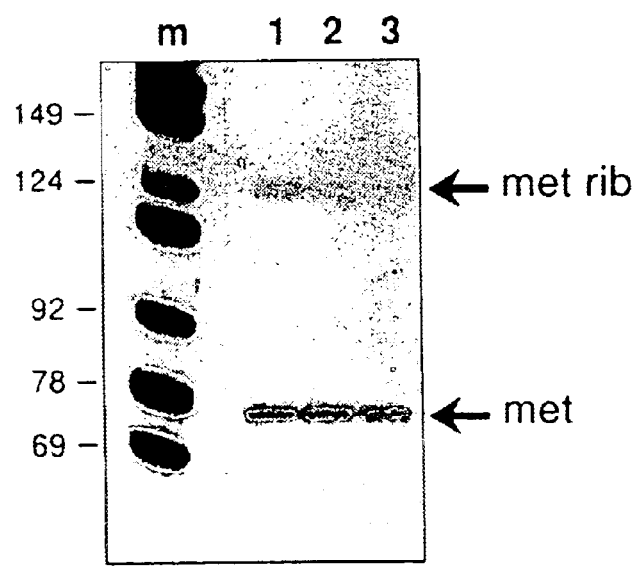

FIG. 5. tRNA ribozyme transcription in Xenopus oocytes.

Lane m: molecular weight marker pBR322, cleaved with HpaII and radioactively labelled using the Klenow fragment of DNA polymerase with alpha $^{32}$P CTP. The molecular weights of some of the fragments (in nucleotides) are shown on the left.

Lanes 1, 2 and 3: the nucleic acid of individual oocytes, injected with the met-tRNA gene and the met-tRNA ribozyme gene metribo 33.

Figure 6:
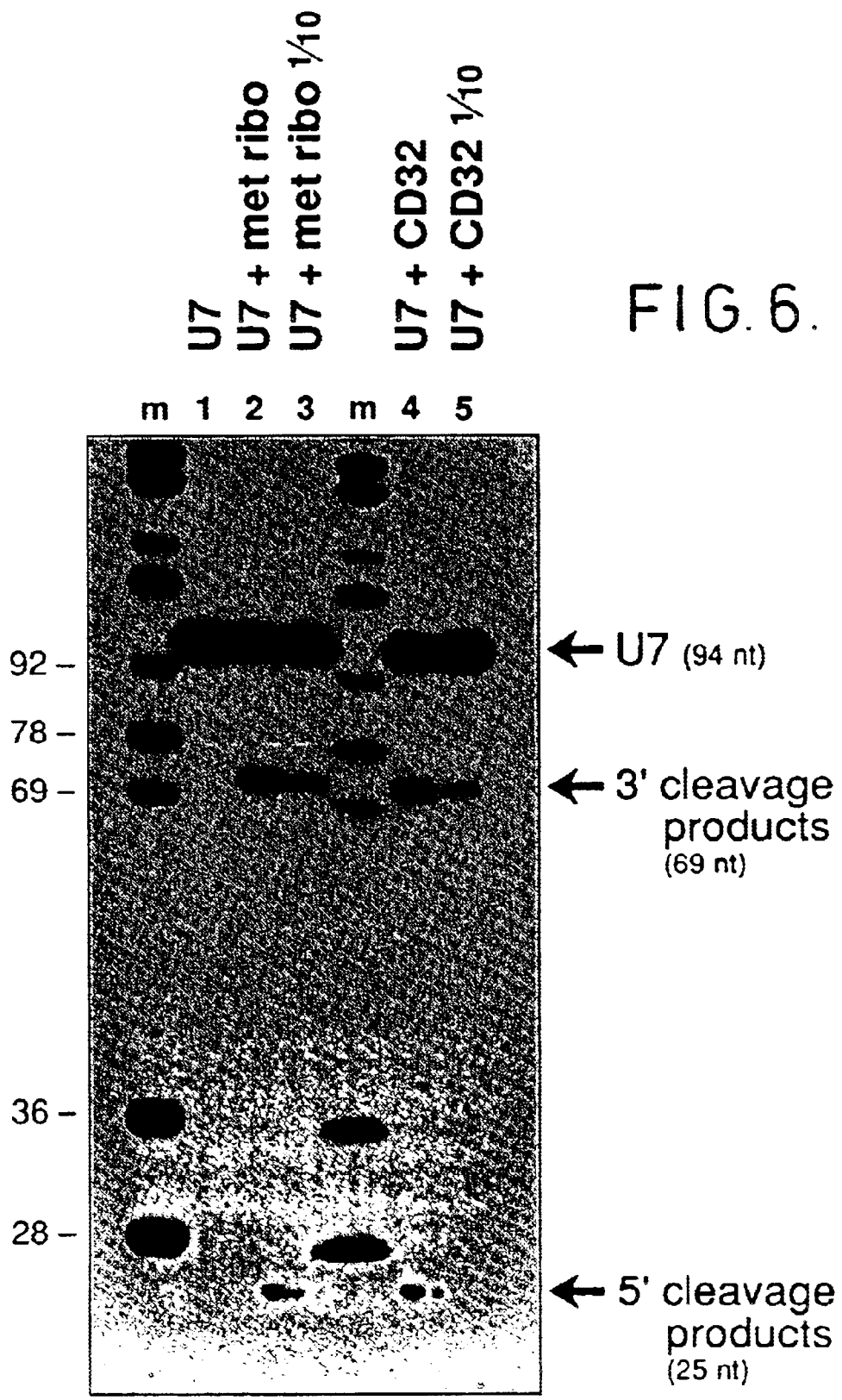

FIG. 6. Comparison of the cleaving activity of ribozyme CD 32 and CD 33.

Lane m: molecular weight marker pBR322, cleaved with HpaII and radioactively labelled using the Klenow fragment of DNA polymerase with alpha $^{32}$P CTP. The molecular weights of some of the fragments (in nucleotides) are shown on the left.

Lane 1: U7-RNA (10,000 cpm, 10 fM), incubated without ribozyme.

Lane 2: U7-RNA (10,000 cpm, 10 fM), incubated with 10 fM of the oocyte-synthesized tRNA ribozyme CD33.

Lane 3: U7-RNA (10,000 cpm, 1 pM), incubated with 10 fM of oocyte-synthesized tRNA ribozyme CD33.

Lane 4: U7-RNA (10,000 cpm, 100 fM), incubated with 10 fM of ribozyme CD32 synthesized in vitro with T7 polymerase.

Lane 5: U7-RNA (10,000 cpm, 100 fM), incubated with 1 fM of ribozyme CD32 synthesized in vitro with T7 polymerase.

Figure 7:
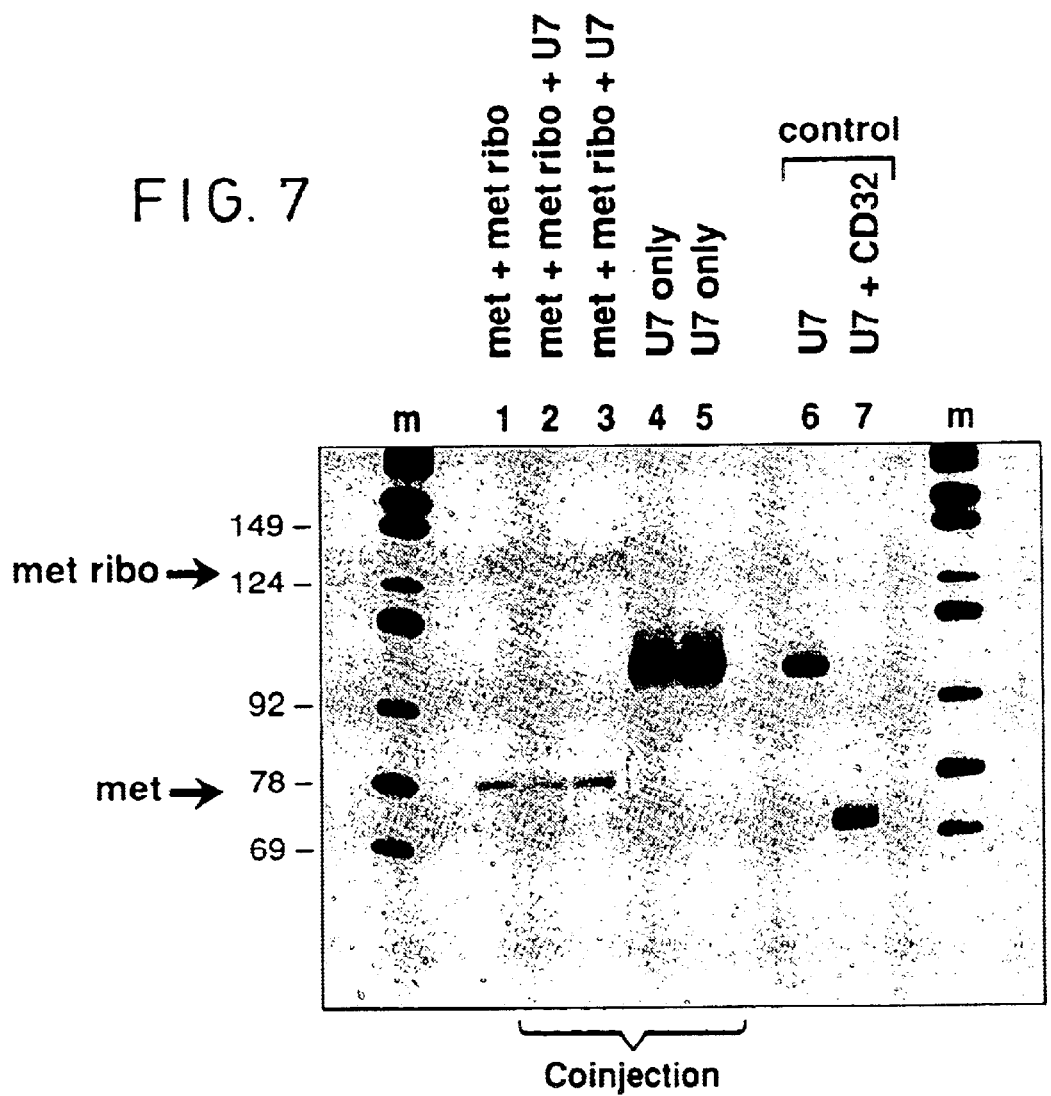

FIG. 7. Cleaving of ribozyme substrate in ocrytes injected with anti-U7-tRNA ribozyme gene and met-tRNA.

Lanes m: molecular weight marker pBR322, cleaved with HpaII and radioactively labelled using the Klenow fragment of DNA polymerase with alpha $^{32}$P CTP. The molecular weights of some of the fragments (in nucleotides) are shown on the left.

Lane 1: nucleic acids from an oocyte injected with the met and metribo genes.

Lanes 2 and 3: oocytes injected with met and metribo, followed by U7-RNA injection.

Lanes 4 and 5: oocytes injected only with U7-RNA.

Lane 6: 1 aliquot of the U7-RNA used for the injection.

Lane 7: U7-RNA (10 fM) incubated with the ribozyme CD32 (10 fM) for 2 hours at 37° C. in the presence of 150 mM NaCl, 10 mM MgCl$_2$ and 20 mM Tris-HCl, pH 7.5. Owing to the gel conditions only the 3' cleavage product (69 nucleotides) is shown.

FIG. 8: Transcription activity of tRNA ribozymes in chicken cells.

Lanes m: molecular weight marker pBR322, cleaved with HpaII and radioactively labelled using the Klenow fragment of DNA polymerase with alpha $^{32}$P CTP. The molecular weights of some of the fragments (in nucleotides) are shown on the left.

Lane 1: antisense ES13 probe, hybridized with *E. coli* tRNA.

Lane 2: antisense ES53 probe, hybridized with *E. coli* tRNA.

Lanes 3 and 4: mapping of the nucleic acids of 10,000 and 100,000 cells which had not been transfected with plasmid DNA hybridized with the ES13 probe.

Lanes 5 and 6: mapping of the nucleic acids of 10,000 and 100,000 cells, transfected with ES13, hybridized with the ES13 probe.

Lanes 7 and 8: mapping of the nucleic acids of 10,000 and 100,000 cells, transfected with ES53, which had been hybridized with the ES53 probe.

FIG. 9: Absorption of DNA by cells treated with transferrin and with transferrin-polylysine.

Lane m: molecular weight marker: pBR322 DNA, cleaved with HpaII and radioactively labeled using the Klenow fragment of DNA polymerase with alpha-$^{32}$P-CTP.

Lane 1: 2000 cpm ES13 fragment.

Lane 2: Material from cells treated with transferrin and ES13.

Lane 3: Material from cells treated with transferrin-polylysine and ES13.

FIG. 10. Erythroblasts incubated with transferrin-polylysine conjugates labelled with FITC have 2 to 10 strongly fluorescing vesicles after 24 hours, which cannot be detected in the controls.

(A) chicken erythroblasts incubated for 24 hours without the conjugate.

(B) chicken erythroblasts incubated for 24 hours with the conjugate and activated in blue light to detect FITC.

(C) the same as (B), but activated with green light which does not allow detection of FITC.

FIG. 11. Wild-type tRNA met and the tRNArib T with the shortened anticodon stem.

FIG. 12. Construction of tRNArib R with the lengthened anticodon stem.

Figure 13:
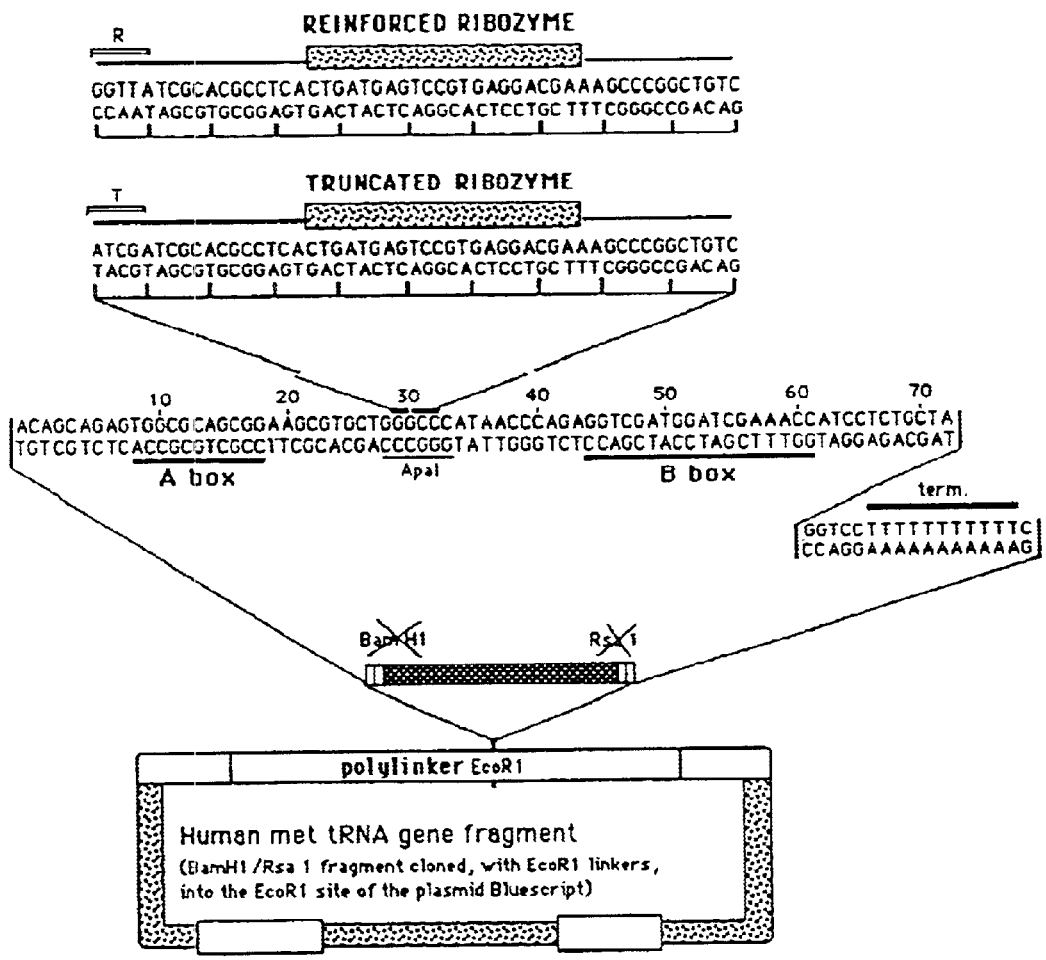

FIG. 13. Sequences of the ribozymes R and T.

Figure 14:
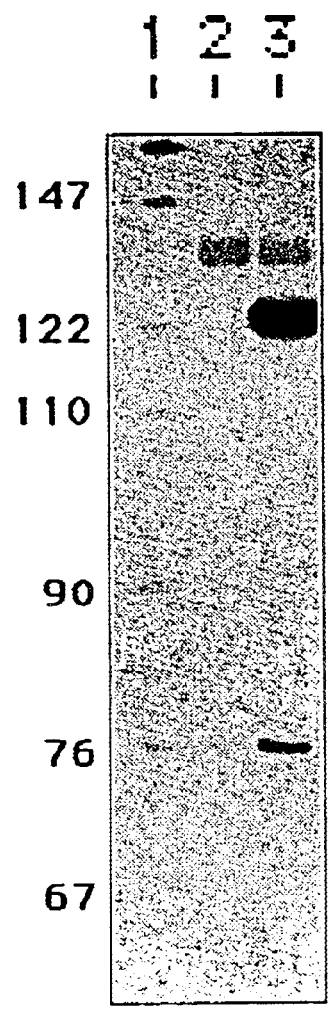

FIG. 14. Xenopus oocytes were injected with ribtRNA genes and incubated for 7 hours. The resulting RNA was harvested, separated by electrophoresis, and visualized by radioautography.

Lane 1: Molecular weight marker.

Lane 2: RibtRNA T (shortened anticodon stem)+ tRNAmet (inj. conc. 10:1).

Lane 3: RibtRNA R (lengthened anticodon stem)+ tRNAmet (inj. conc. 10:1).

FIG. 15. Structure of Xenopus oocyte tRNAtyrC; structure of tRNAtyrM, complementary to the anticodon triplet and modified to contain an ApaI restriction site.

Figure 16:
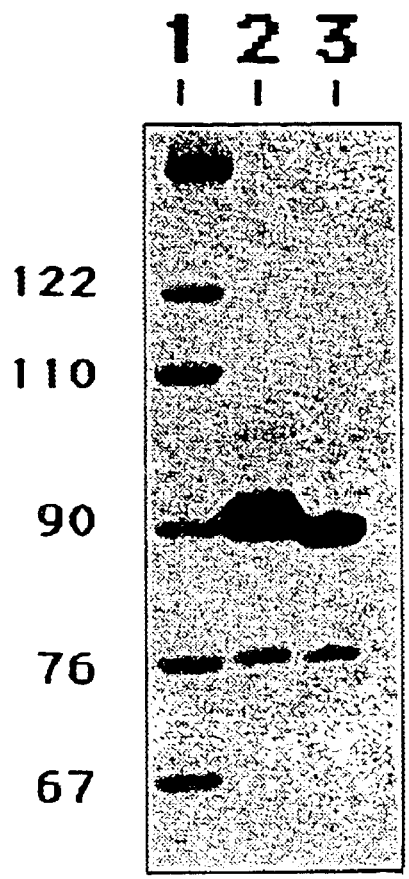

FIG. 16. Comparison of activity of modified gene (tRNAtyrM) with wild-type gene in Xenopus oocytes.

Lane 1: Molecular weight marker.

Lane 2: tRNAtyrM+5S RNA (inj. conc. 50:1).

Lane 3: tRNAtyrC+5S RNA (inj. conc. 50:1).

Figure 17:
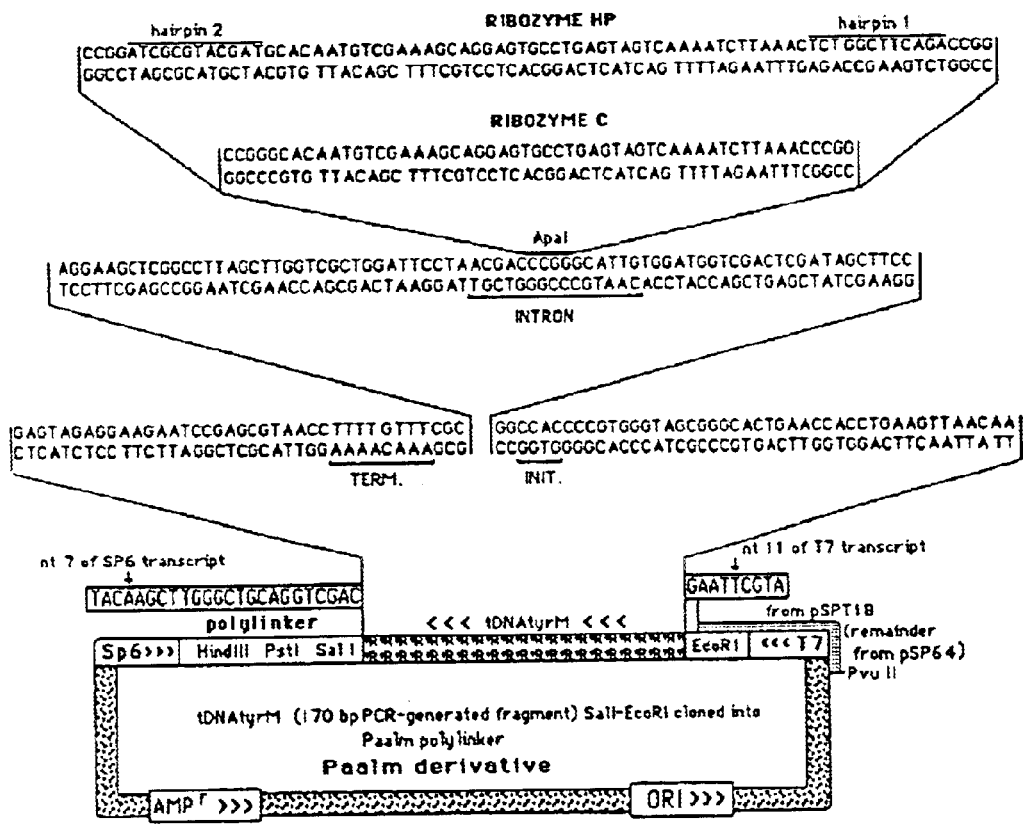

FIG. 17. Two oligodeoxyribonucleotides which contained ribozyme sequences were synthesized, which already contain ApaI ends and could be cloned directly into the intron sequence of the modified tRNAtyr gene. 12 nt were inserted at both ends of one gene in order to form stable "hairpins" in ribintrons and counteract the degradation by exonuclease. The overall size of the resulting introns was 80 nt (ribozyme HP) as compared to 65 nt in the case of the unprotected ribozyme sequence (ribozyme C). The sequences of the ribozymes and the cloning plan are shown in the figure.

Figure 18:
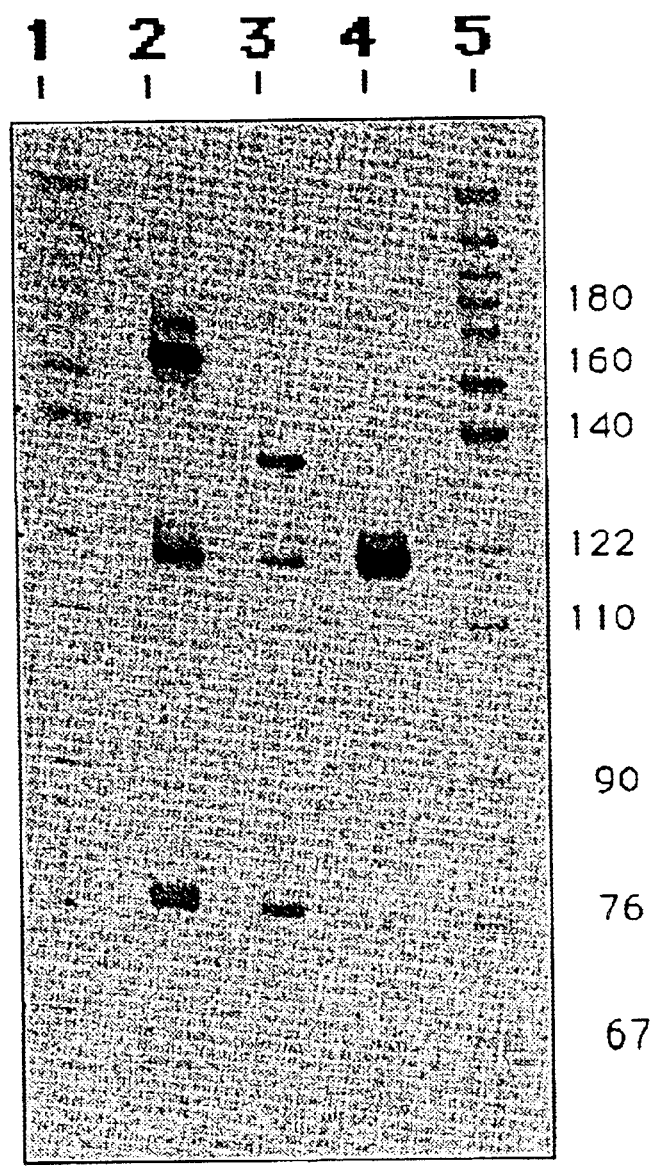

FIG. 18. Transcription of constructs HP, C and D.

Lanes 1 and 5: Molecular weight marker.

Lane 2: RibtRNA HP+5S RNA (inj. conc. 20:1).

Lane 3: RibtRNA C+5S RNA (inj. conc. 1:1).

Lane 4: RibtRNA D+5S RNA (inj. conc. 20:1).

DETAILED DESCRIPTION OF THE INVENTION

The idea which served as a starting point for the solution to this problem was the fact that, by introducing a gene which produces the inhibiting RNA, as against importing the RNA as such, considerable amplification of the RNA would be ensured and consequently there would be a supply of RNA sufficient to inhibit the biological reaction.

The inhibiting RNA may be any desired ribozyme or another mRNA-inhibiting RNA, e.g. an antisense RNA. Theoretically, it would be possible to carry out efficient transporting of RNA or the DNA sequence coding for it by means of viruses or viral vectors such as retroviruses.

However, this system has some serious disadvantages, such as the mobilization of endogenous viruses, recombination with endogenous retroviruses, activation of endogenous genes by integration, restriction with regard to host organism and type of tissue.

By contrast, therefore, carrier genes are prepared according to the invention which do not have these disadvantages.

The genes proposed as carrier genes for RNA genes within the scope of the present invention have the following advantages; they have a compact structure, they are easier to transport in the cell, being smaller in size, they have a high transcription rate and are not restricted to specific tissues in their expression but are expressed ubiquitously, i.e. in virtually all types of cell.

A further advantage of the polymerase III genes is the presence of a very powerful transcription termination signal. This reduces the probability of a nearby cellular gene being undesirably activated.

The genes transcribed by the polymerase III have the following features: they are genes wherein the promoter is not located upstream in front of the gene but is inside the gene (Geiduschek et al., 1988). These internal control regions which are essential for the binding of the polymerase III have a discontinuous structure; they consist of two so-called boxes (the A box and B box) which are essential for recognition by the transcription factors, and an intermediate gene section the length of which is critical (Hofstetter et al., 1981). The length of this sequence is 31 to 74 base pairs in tRNA genes. (Clarkson).

Examples of these genes which are transcribed by polymerase III are the tRNA genes, 5S-RNA and a number of other small nuclear and cytoplasm RNA genes: 7SK, 7SL, M, U6 and 4,5S RNA, as well as the adenovirus genes VA1 and VA2 (Geiduschek et al., 1988). Something common to these genes is their reduced size, compact structure, high transcription rate and ubiquitous transcription.

It has surprisingly been found that using the genetic units according to the invention it is possible to achieve increased stability of the inhibiting RNA without having to accept a reduction in their effectiveness in terms of activity.

It has already been shown by Jennings and Molloy, 1987, that a promoter recognised specifically by polymerase III is suitable for guiding the synthesis of antisense RNA. For this purpose, the XbaI/BamHI fragment of the VA1 gene, containing the promoter, was cloned in the 5' direction in front of the antisense DNA, corresponding to the conventional principle when using polymerase II promoters. Endeavours were made to obtain a transcript which was short in comparison with polymerase II transcripts. The transcript has only one slight modification which makes base-pairing of the ends possible in order to protect the ends from digestion by single strand exonucleases.

In contrast to this suggestion, in which only the promoter sequence of a specific polymerase III gene is used (the region between positions 30 and 73, whereas the wild-type VA1 gene extends as far as the terminator sequence at positions +160 to +200), according to the present invention those sequences of the polymerase III gene which determine the secondary structure of the transcript are additionally used in controlled manner in order to exploit them for stabilising the inhibiting RNA sequences. In contrast to the proposal described above, the genetic sequence coding for the inhibiting RNA is arranged inside the gene transcribed by polymerase III so as to obtain, according to the invention a "gene cassette". Furthermore, the carrier genes used in the present invention are non-toxic, unlike the viral VA1 gene.

The genes transcribed by polymerase III can be used flexibly within the scope of the invention. With respect to their function as carrier genes for RNA-inhibiting sequences, the following criteria should be considered when selecting or modifying natural genes or artificial genes during construction:

1) the A and B boxes are highly conserved.
2) a section of 5 to 7 T residues downstream of the B box is responsible for terminating the transcription.
3) the distance between the A and B boxes cannot be enlarged at will, the maximum spacing currently being assumed to be about 90 bp.
4) in some systems, the 5' flanking sequence has an influence on transcription.
5) there are indications that an intact anticodon stem region is responsible for the stability of the transcript.

tRNA genes are particularly suitable as carrier genes for the production of the genetic unit according to the invention. The RNAs coded by these genes are also regarded as particularly suitable for stabilising the inhibiting RNA, owing to their clover leaf structure. Using these genes, it is possible to produce compact RNA-producing genetic units, by inserting the sequence which codes for the inhibiting RNA between the A and B blocks (FIG. 1 shows a diagrammatic representation of a tRNA ribozyme gene).

Experiments within the scope of the present invention were carried out using the start methionine-tRNA, which has an ApaI restriction site in the anticodon stem and loop region located between the A and B blocks (the start methionine-tRNAs of all higher eukaryotes have this restriction site in the anticodon loop).

In addition to the region located between the A and B blocks other insertion sites are also possible within the carrier DNA sequences (tRNA genes or other polymerase III genes), provided that care is taken to ensure that the transcription activity of the polymerase III and the stability of the transcript are maintained.

However, theoretically, the genetic units according to the invention may be produced with all tRNAs; if necessary, a suitable restriction site may be constructed, into which the sequence coding for the inhibiting RNA is then inserted. The only condition is that during insertion no base exchange must be allowed in the anticodon base region which will affect the transcription rate of the gene or the stability of the resulting tRNA (Folk et al., 1983). Furthermore, it must be born in mind that inserts larger than 60 bp may effect the transcription (Ciliberto et al., 1982).

With regard to the choice of suitable carrier genes it is fundamentally desirable to use tRNA genes of the same species or other genes transcribed by polymerase III which are not toxic.

The experiments within the scope of the present invention were carried out by introducing ribozyme sequences into normal tRNA genes. If the tRNA ribozyme transcribed by this gene is located primarily in the cytoplasm but it is desirable for specific applications, e.g. in order to inhibit nucleus-specific RNAS, e.g. those from snRNP particles, to locate the tRNA ribozyme or the tRNA ribozyme or tRNa antisense RNA in the nucleus, it is possible to use mutants which are located predominantly in the nucleus, e.g. the met i tRNA gene described by Zasloff et al., 1982 and by Zasloff, 1983, which has a single base exchange.

The genetic units according to the invention may be prepared as follows, for example:

A copy of the gene transcribed by polymerase III, e.g. a tRNA gene, contained on a bacterial plasmid, is cleaved with a suitable restriction enzyme at the site provided for insertion, e.g. Between the A and B blocks, and the double stranded DNA produced by conventional methods, which codes for the inhibiting RNA, is ligated therein. Suitable host organisms are transformed therewith, selected, replicated and the amplified plasmid-DNA is obtained. The plasmids are checked for the presence of the genetic unit according to the invention; this can be done by restriction digestion, sequence analysis or by detecting a functional in vitro transcript of the plasmid DNA.

The genetic units thus obtained may be used both in the form of the circular plasmid and also in the form of the genetic unit cut out of the plasmid, which contains all the information required for the transcription by polymerase III.

The particular form chosen would generally depend on the field of use and on the transport system selected for introducing the genetic unit into the cell.

The genetic units according to the invention may occur as multiple copies (tandem structures in which the genetic units are arranged one behind another, with the inhibiting inserts being identical or different).

Transcription of a tandem of this kind yields separate RNA units, owing to the promoter and termination signals contained in each individual unit. The orientation of the individual units with one another is also irrelevant owing to this property of the fragments to occur as complete transcription units. When producing such tandems, plasmids are used which contain multimeric copies of the region coding for the inhibiting units. Vectors which contain multimeric tRNA ribozymes genes may be produced, for example, starting from the erbB-cut series described in example 1, by ligating the individual fragments using T4 DNA ligase to produce polymers and recloning the polymeric genes into a corresponding restriction site of a suitable plasmid vector. The production of such tandems is made possible by the small size of the units according to the invention, which preferably amount to 200 to 350 bp. Using a tandem inhibitor of this kind, after the preparation of a heteromeric complex of antisense RNAs or ribozymes, the effectiveness of the set of inhibitors can be tested in a single experiment. For example, a mixture of 5 to 10 ribozymes can be introduced into a cell system using this method. After inhibition has occurred as a result of the mixture, the individual ribozymes can be tested for their activity. This is particularly advantageous owing to the fact that the criteria for selecting target RNA sequences which are to be inhibited have not yet been thoroughly investigated.

Good target sequences include, for example, those regions which have no secondary structure, regions near cleavage signals, regions following the initiation codon, regions without binding sites for specific proteins (such as for example the Sm binding site in snRNA molecules). Using the present invention, particularly in tandem form, it is possible to come to some conclusions regarding these target sequences and consequently to inhibit them efficiently.

The use of tandem units is also advantageous when it is necessary to cleave the RNA, e.g. viral RNA, at several sites in order to inactivate biological processes. Multiple cleaving can be achieved for example by constructing a fairly large number of different ribozymes and introducing a vector containing the genetic units with the DNA sequences coding for them into cells. When these sequences are transcribed, the ribozyme units are added to the corresponding target sequences, as a result of which the mRNA is split into fragments.

Multimeric copies can be used when larger quantities of a low molecular ribozyme are required for achieving satisfactory results in specific applications, for example when using the transferrin-polycation transport system. Plasmids which carry multimeric copies of the genetic unit and which contain the DNA sequence coding for this ribozyme improves the production of the fragment by increasing the yield to a multiple of what it was.

Tandem units can also advantageously be used when it is simultaneously desired to produce inhibiting RNAs directed against various types of RNA.

When the invention is applied to antisense RNA care must be taken to limit the size of the insert, in the case of tRNA genes. For efficient transcription the order of magnitude is about 60 bp; therefore, when larger antisense-RNA constructs are used, other genes transcribed by polymerase III which have larger capacity, with a view to transcribing longer sequences, should be considered.

The carrier genes which can be used within the scope of the invention may also be produced synthetically, provided that they meet the condition of having the transcription units necessary for transcription by polymerase III. The use of such synthetic genes may bring the following advantages:

a) such genes are not Kepognised by aminoacyl-synthetases and by ribosomes and consequently interference with the translation machinery of the circle is avoided.

b) there is the possibility, by creating synthetic constructs, of producing inhibiting RNAs with a greater stability and higher transcription rate than are obtained with a natural gene.

c) the cloning process can be made more flexible by the creation of synthetic sequences.

It has been established, within the scope of the present invention, that the stability of the ribozyme-tRNA molecules can be increased by lengthening the anticodon base region of the carrier tDNA molecule. It has been demonstrated that, by lengthening the anticodon base region of the wild-type tRNA gene, which has 5 base pairs, to a total of 9 base pairs, it is possible to obtain six times as much transcript compared with the shortened wild-type tRNA gene, and this can be put down to an increase in stability and the processability which can be obtained as a result.

It has also been established that an increase in the stability of the genetic units according to the invention in the form of tRNA-ribozyme genes or tRNA-antisense genes can also be achieved if the DNA sequences coding for the inhibiting RNA function are present as parts of introns (known as "ribintrons" in the case of ribozymes). The starting premise was that naturally occurring introns do not change the secondary structure of tRNA precursor molecules and the tRNA introns show no sequence conservation, and consequently, by claiming ribozyme or antisense sequences as part of introns, the structural changes in the resulting tRNA precursor are minimised and the stability is consequently maximised. By means of the tyrtRNA gene used according to the present invention, wherein the splicing of the tRNA precursor molecules is effected only slowly, it is possible to demonstrate that by using tDNA molecules which contain "ribintron" sequences the activity of ribtRNA can be effectively increased. It is then possible to launch a more powerful attack on RNAs located in the cytoplasm. This system provides a simple method of incorporating suitable structural elements for increasing the stability of the "ribintrons" against degradation by exonucleases. This may be achieved for example by additional base-pairings or by larger hairpin regions adjoining the ribozyme sequences. In modifications of this kind it must be ensured that the structures which are crucial to the splicing of the intron are maintained.

The natural intron sequences can be modified, e.g. by the insertion of suitable restriction cutting sites, in order to permit the cloning of oligonucleotides or, if they are not already contained in the naturally occurring gene, by the insertion of nucleotides which permit base pairing with the anticodon triplet, in order to make available an additional stabilising structural feature.

It has been shown, within the scope of the present invention, that the expression of ribozymes as a constituent of introns does not essentially involve any deterioration in the tRNA secondary structure, and consequently the transcript produced can be accumulated in high concentrations and processed correctly. If the intron released during processing proves to be insufficiently stable, suitable structural features can be provided which will increase the stability to exonuclease degradation.

A number of methods may be used to introduce the genetic units according to the invention into the cells:

The standard method of inserting DNA into tissue culture cells makes use of the formation of a co-precipitate between the DNA and calcium phosphate (Graham et al., 1973). The precipitate is added to cells which take up a certain amount, possibly by a pinocytosis process. A similar method uses a positively charged material, DEAE-dextrane, which makes it easier for DNA to be absorbed by the cell. Methods have also been developed in order to introduce DNA into the cell by electroporation (in which pores are temporarily produced by a pulsating electrical field) (Langridge et al., 1987, Fromm et al., 1987). Microinjection techniques for introduction into large cells (Kressmann et al., 1980) and tissue culture cells (Perpperkok et al., 1988) can also be used. However, these methods are only suitable for laboratory use or for in vitro applications. Recently, a synthetic cationic peptide (DOTMA) was developed which spontaneously forms liposomes with DNA and thus makes it easier for the DNA to be carried into the cells (Felgner et al., 1987). Theoretically, as already mentioned, retroviral vectors are also suitable for the transfer of genetic material into the cell (Stewart et al., 1986, 1987); however, these systems have the disadvantages already mentioned.

Another transporting mechanism is based on the use of "disarmed" toxins as transporting vehicles.

The methods of transport used hitherto all suffer from the defect of being unable to convey sufficient inhibiting nucleic acid into the cell. With the aid of the present invention it is now possible, owing to the smallness and compact nature of the molecules, to increase the number of active inhibitor units in relation to the transporting capacity. Because of the small size and compact structure of the genetic units according to the invention, after slight modifications, e.g. conjugation with cholesterol, lipophilic counter-ions or nucleus locating peptides, there is no need for a transporting system at all.

Preferably, within the scope of the present invention, a soluble system is used for transportion, using receptor-mediated endocytosis. It is particularly preferable for a transferrin-polycation conjugate to be complexed with the genetic unit according to the invention; the complex is taken up by the transferrin receptor, which is present on virtually all growing cells.

The fields of application for the present invention are numerous: e.g. transgenic animals can be produced which, because of the presence of the genetic units according to the invention in their genetic material, will have an intracellular immunity to viruses, e.g. foot and mouth virus, Newcastle Disease virus, bovine papilloma virus, pseudorabies or infectious gastroenteritis. Accordingly, intracellular immunity, e.g. against the potato virus PVX, can also be produced in transgenic plants. Furthermore, the genetic units according to the invention may also be introduced into somatic cells in order to use ribozymes or antisense-RNAs directed against pathogenic viruses such as HIV or related retroviruses in order to fight these viral pathogens.

Another field of use is in gene therapy by the use of RNA constructs with complementarity to oncogenes or other key genes which control the growth and/or differentiation of cells. In such applications, the high specificity of RNA inhibition which can be effectively achieved with the aid of the present invention and by means of which it is possible to distinguish, for example, between protooncogene and oncogene transcripts, acquires some importance.

Moreover, the genetic units according to the invention may be used in this way to prevent the expression of specific genes in plants or animals, in order to bring out desirable characteristics.

The inhibitory effect of RNA can also be used to combat diseases so that the production of undesirable genetic products is suppressed, e.g. the production of the major plaque protein which occurs in Alzheimer's Disease or the proteins which cause autoimmune diseases.

The present invention may also be applied in those cases in which the regulatory protein which interacts with RNA is supposed to be eliminated by the addition of RNA.

The invention also includes pharmaceutical preparations which contain the genetic units according to the invention as their active component, possibly in the form of lyophilised materials. The use thereof covers the ranges of indications specified above.

Using the experiments carried out within the scope of the present invention it was possible to demonstrate the transcription activity of the tDNA ribozyme gene. To do this, a tDNA ribozyme gene construct was prepared by inserting a DNA sequence coding for a 53 bp long ribozyme directed against the snRNA U7 sequence into the ApaI restriction site between the A box and B box of the start methionine tDNA (the A box and B box are the two recognition sequences for the polymerase; transcription begins 15 bp upstream of the A box and ends at an oligo T sequence downstream of the B box). After microinjection of this gene, transcription was detected; the concentration of the tRNA/ribozyme hybrid was 10 to 20% of the concentration of tRNA, which was produced by a co-injected wild-type tRNA gene.

RNA molecules, synthesized in vitro from the tRNA ribozyme gene, cleave the target RNA at the site envisaged. The addition of the tRNA structure to the ribozyme sequence does not block the ribozyme activity. tRNA ribozyme molecules synthesized from genes which have been injected into oocytes also cleave the target RNA at the site envisaged and with the same effectiveness as ribozymes synthesized in vitro without the additional tRNA structure. This proves that in vivo synthesis and processing of a tRNA ribozyme are not accompanied by modifications which interfere with the activity of the ribozyme.

Within the scope of the present invention, the activity of a ribozyme has been detected in vivo for the first time. To do this, tDNA/ribozyme genes together with radioactively labelled GTP were injected into the nucleus of oocytes. After 8 hours incubation which was provided for the synthesis of ribozyme, the radioactively labelled substrate RNA (U7 RNA) was injected into the cytoplasm of the oocytes. After another 2 hours, the nucleic acid was removed from the oocytes: in the oocytes in which ribozyme synthesis had taken place, no remaining substrate RNA could be detected. By contrast, in those oocytes which had not been injected with the tDNA/ribozyme gene or in which the gene had missed the nucleus, the substrate RNA was stable.

Within the scope of the present invention it was also possible to demonstrate that the tDNA ribozymes according to the invention are capable of inhibiting the transforming effect of an oncogene. Using erythroid chicken cells, transformed with the erbB oncogene, the activity of a tRNA ribozyme was detected by means of the differentiation of the cells in erythrocytes which occurred as a result of inhibition of the erbB expression.

The efficacy of the genetic units according to the invention can also be tested by observing the resistance of mouse cells to infections, e.g. polyoma infections, after the use of genetic units according to the invention which are directed against the virus (possibly against several regions), e.g. against the papilloma virus.

EXAMPLE 1

Construction of tRNA ribozyme genes.

a) Construction of pSPT18met1

The methionine initiator 1-tRNA gene of xenopus, present on a 284 bp EcoRI fragment which was cloned in pBR322 (the HinfI H-G fragment (Hofstetter et al., 1981, Tellford et al. 1979), was isolated by EcoRI digestion of the pBR322 vector, purified by gel electrophoresis (2% agarose/TBE) and ligated into the EcoRI site of the bacterial plasmid pSPT18 (Boehringer Mannheim) in such a way that when the plasmid was transcribed with SP6 polymerase a sense-tRNA transcript was obtained. Standard cloning method as described in (Maniatis) were used for this purpose. The main advantage of the recloning of the tRNA gene in pSPT18 consists in the presence of opposing SP6 and T7-RNA polymerase promoters in the plasmid. Therefore, by in vitro transcription it is possible to obtain specific RNA transcripts which contain either the tRNA ribozyme sequence or the complementary sequence (Melton et al., 1984). These transcripts are useful for testing the cleaving activity of the RNA molecule or for detecting the presence of tRNA ribozymes in cell extracts which express the tRNA ribozyme, by "RNase Protection Mapping".

b) Construction of tRNA Ribozyme Genes

Figure 2:
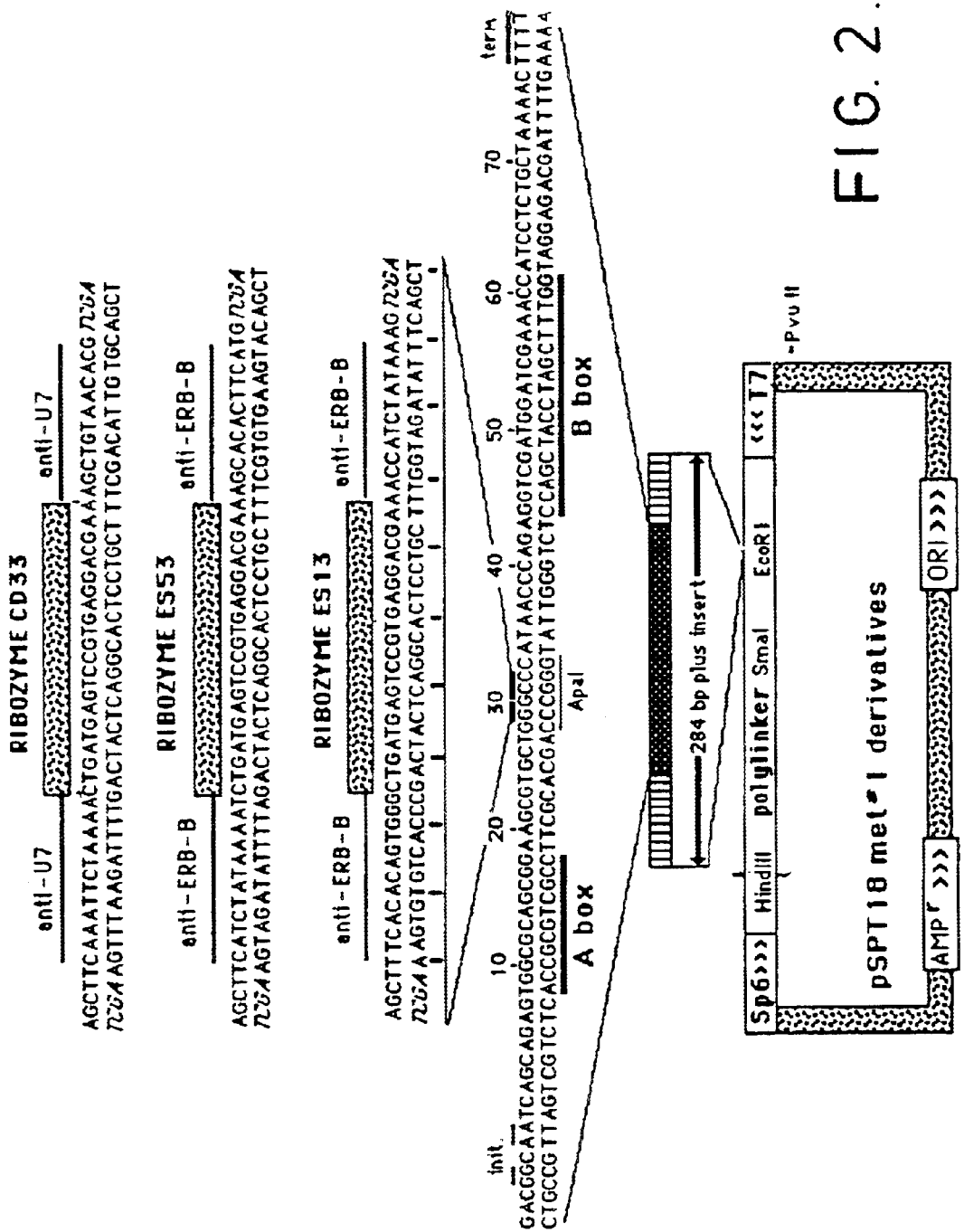
FIG. 2. This figure shows plasmids which contain the sequences coding for tRNA ribozyme. pSPT18met1 contains the 284 bp EcoRI fragment which carries the *Xenopus laevis* initiation tRNA gene. This is the G-H fragment cloned into the EcoRI site of the polylinker of pSPT18. The complementary oligonucleotides coding for ribozymes which are directed against U7snRNA are shown. The cloning strategy used here resulted in the removal of the projecting ends of the ApaI site in the tRNA gene. The part of the insert coding for the ribozyme and the regions complementary to the target RNA (anti-U7, anti-erbB) is marked, as are the A and B boxes, the section of the 5T residues (termination signal) and the transcription initiation sites. The plasmid contains the ColEI replication origin, and ampicillin resistance marker and the promoters for 17 and SP6-RNA polymerase.

The tRNA gene on pSPT18met1 was cleaved at the single ApaI site in the anticodon stem and loop region (see FIG. 2). This figure shows plasmids which contain the sequences coding for tRNA ribozyme. pSPT18met1 contains the 284 bp EcoRI fragment which carries the *Xenopus Laevis* initiator tRNA gene. This is the G-H fragment (Hofstetter et al., 1981), cloned into the EcoRI site of the polylinker of pSPT18. The complementary oligonucleotides coding for ribozymes which are directed against U7snRNA (CD33 and the two sequences of the erbB-mRNA (ES13, ES53), are shown. The cloning strategy used here reverted in the removal of the projecting ends of the ApaI site in the tRNA gene. The part of the insert coding for the ribozyme and the regions complementary to the target RNA (anti-U7, anti-erbB) is marked, as are the A and B boxes, the section of the 5 T residues (termination signal) and the transcription initiation sites. The plasmid contains the ColEI replication origin, and ampicillin resistance marker and the promoters for T7 and SP6-RNA polymerase.

Figure 4:
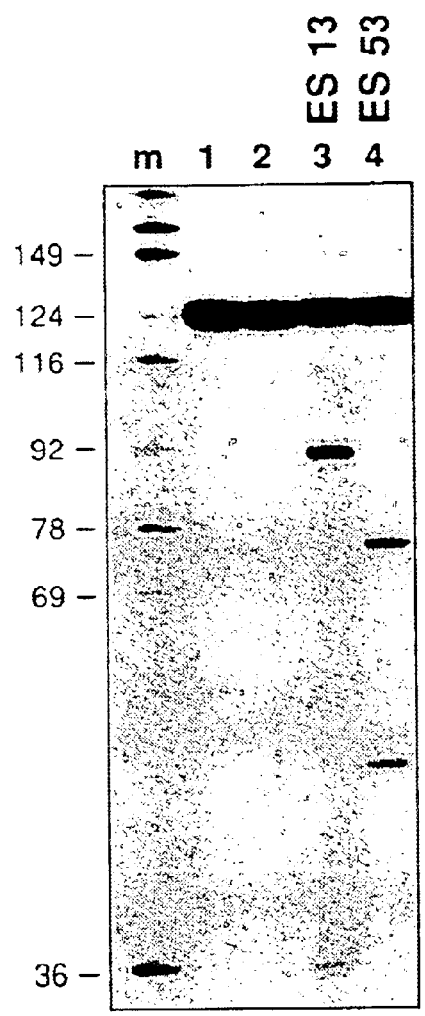
FIG. 4. The in vitro ribozyme activity of the tRNA ribozymes is shown.

In order to produce double-stranded synthetic DNA oligonucleotides coding for the viroid cleavage sequence (Haseloff et al., 1988) flanked by the sequences which are complementary to the target mRNA, first of all single-stranded oligonucleotides were produced according to standard methods (Applied Biosystems DNA synthesizer). Complementary oligonucleotides were phosphorylated, annealed and ligated into the ApaI-cleaved pSPT18met1 plasmid using standard methods (Maniatis). The ligation mixture was used to transform *E.coli* HP101, bacterial clones containing the new plasmid were isolated and the presence of active ribozyme sequences on the bacterial plasmid was confirmed by two methods:

1) RNA molecules originating from the in vitro SP6 transcription of cloned DNA plasmids were incubated with a radioactively labelled RNA containing the target sequence for the ribozyme and tested for specific cleaving of the target RNA (see FIG. 4).

2) the presence of correctly inserted DNA sequences was confirmed by dideoxy-DNA sequencing by means of the insertion site.

FIG. 4 shows the in vitro ribozyme activity of the tRNA ribozymes. Plasmid DNA molecules which carried the erB-cut tRNA ribozymes ES13 and ES53 were digested with PvuII and transcribed with SP6-RNA polymerase. This transcription yielded RNA molecules 230 nucleotides long, containing the tRNA ribozyme sequence and in addition the 5' and 3' flanking sequences which originate from the flanking xenopus sequences and the flanking bacterial plasmid sequences (see FIG. 2). The ribozyme transcripts were incubated with 20,000 cpm (20 fM) of an RNA molecule with the region of the erbB-mRNA including the initiation codon. The RNA molecule has the target sequences both for ES13 and ES53 (see FIG. 3). After 2 hours incubation of the ribozyme plus target RNA at 37° C. in the presence of 10 mM $MgCl_2$, 20 mM Tris-HCl, pH 7.5 and 150 mM NaCl, EDTA was added to a concentration of 15 mM, the sample was dried, dissolved in 80% formamide/TBE, heated to 95° C. for 30 seconds and separated on a 9.5% acrylamide/8.3 M urea/TBE gel. After electrophoresis, the labelled RNA molecules were detected by autoradiography.

Lane M: molecular weight marker: pBR322 DNA, cleaved with HpaII and radioactively labelled using the Klenow fragment of DNA polymerase with alpha $^{32}p$ CTP (Maniatis). The molecular weight markers were dissolved in 80% formamide/TBE immediately before being applied to the gel and heated to 95° C. for 3 minutes. The molecular weights of some of the fragments (in nucleotides) are shown on the left.

Lane 1: erbB-target mRNA (20,000 cpm, 20 fM) without incubation.

Lane 2: erbB-target mRNA (20,000 cpm, 20 fM) incubated with $MgCl_2$ at 37° C. without ribozymes.

Lane 4: erbB-target mRNA (20,000 cpm, 20 fM) incubated with ES13-RNA (1 fM).

Lane 5: erbB-target mRNA (20,000 cpm, 20 fM) incubated with ES53-RNA.

Figure 3:
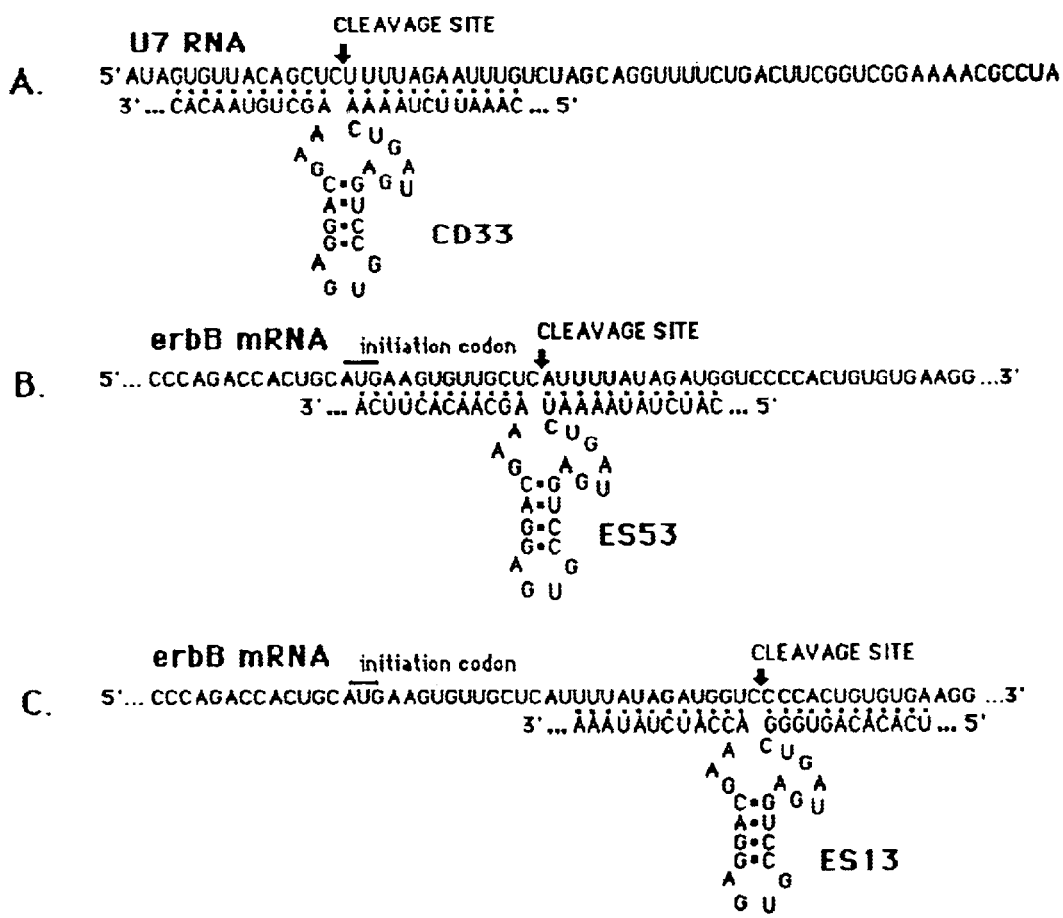
FIG. 3. The complementarity between ribozymes and target RNAs are shown.
(A) CD33 against U7snRNA.
(B) ES53 against erbBmRNA.
(C) ES13 against erbBmRNA.

On the right of the figure the molecular weights (in nucleotides) of the erbB target mRNA and the 5' and 3' cleavage products of both ribozymes splitting reactions are given (see also FIG. 3).

FIG. 3 shows the complementarity between ribozymes and target RNAS: CD33 (A) against U7snRNA cotten et al., 1988, ES13 (C) and ES53 (B) against sequences of erbBm-RNA (Venustrom et al., 1980).

The tRNA part of the tRNA ribozymes is not shown, for the sake of clarity. The cleavage sites for the ribozyme are marked, as are the initiation codons of the erbB-mRNA.

EXAMPLE 2 tRNA ribozyme transcription in xenopus oocytes.

The transcription of the tRNA ribozyme genes, microinjected into xenopus oocytes, was carried out using the method described for tDNA in Kressmann et al., 1978, Hofstetter et al., 1981, Kressmann et al., 1980. The following procedure was used: Stage VI oocytes were obtained from HCG (Human Chorionic Gonadotropin)-stimulated adult *Xenopus Laevis* females. The oocytes were briefly centrifuged in order to bring the nucleus to the edge of the oocytes. Each nucleus was injected with about 50 nl of a solution containing 0.3 µg/µl of supercoiled plasmid DNA (containing the tRNA ribozyme gene according to Example 1) and 2 µCi/µl of $^{32}$P-GTP. After 5 to 8 hours incubation at 20° C. the individual injected oocytes were digested for 45 minutes at 37° C. in 1% SDS, 1 mg/ml of Proteinase K, 300 mM NaCl. 20 mM Tris, pH 8, 20 mM EDTA (400 µl/oocyte), extracted once with phenol and once with phenol/chloroform and precipitated with ethanol. The collected ethanol precipitates were dissolved in 80% formamide/TBE, briefly heated to 95° C. in order to-denature them and separated by electrophoresis on a 10% acrylamide/8.3 M urea/TBE gel and made visible by autoradiography. In all the experiments with tRNA ribozyme genes the injection solutions contained the wild-type metRNA genes with a concentration of 1/6 of the concentration of the tRNA ribozyme gene. TBE buffer (Tris, borate, EDTA) was prepared according to the. instructions described in (Maniatis).

The results of these experiments are shown in FIG. 5:

Lane m: molecular weight marker: as in FIG. 4. The molecular weights of some of the fragments (in nucleotides) are shown on the left of the drawing.

Lanes 1, 2, 3: the nucleic acid of individual oocytes, injected with the met-tRNA gene and the met-tRNA ribozyme gene metribo 33. On the right of the drawing the positions of the met tRNA (met, 77 nucleotides long) and of the tRNA ribozyme (metribo), 128 nucleotides long) are given.

EXAMPLE 3

Determining the ribozyme activity of tRNA ribozyme synthesized from oocytes by comparison with ribozyme synthesized in vitro which contains no tRNA sequences.

A tRNA ribozyme directed against U7 and synthesized in microinjected oocytes was obtained by separation using electrophoresis, made visible by autoradiography, cut out of the polyacrylamide gel and eluted by incubation overnight in an Eppendorf Vibrator in HEP (Heidelberg Extraction buffer: 0.75 M ammonium acetate, 10 mM magnesium acetate, 1% (vol./vol.) phenol, 0.1% (weight/vol.) SDS, 0.1 mM EDTA). The eluted RNA was extracted once with phenol/chloroform and once with chloroform and precipitated with ethanol in the presence of 10 µg *E.coli* tRNA as carrier. The precipitate was taken up and quantitatively determined by Cerenkov counting of the $^{32}$P-labelling using the values for the specific activity (Kressmann et al., 1982). Samples of the tRNA ribozyme were incubated with $^{32}$P-labelled RNA containing the U7 sequence (10,000 cpm/sample, 10 fM plus the stated quantities of unlabelled U7-RNA) for 2 hours at 37° C. in the presence of 150 mM NaCl, 10 mM $MgCl_2$ and 20 mM Tris HCl, pH 7.5. The reaction was stopped by the addition of EDTA to 15 mM, the samples were dried, dissolved in 80% formamide/TBE, heated to 95° C. for 30 seconds and separated on a preheated 9.5% acrylamide/8.3 M urea/TBE gel. The radioactively labelled types of RNA were made visible by autoradiography at −80° C. with a Dr. Goos "special" intensifying film.

The ribozyme CD32 was obtained by T7 polymerase transcription of a plasmid containing the insert of CD33 (see FIG. 2) and cloned into the Hind III/sal I sites of pSPT19 (Boehringer Mannheim). This transcript contains only the ribozyme sequence plus the sequences complementary to U7, flanked by short sections of the vector sequence. The cleaving activity of this ribozyme was used as a comparison with the cleaving activity of the oocyte-synthesized tRNA ribozyme CD 33, in order to assess the influence of the secondary structure of the tRNA and of the in vivo synthesis and modification on the ribozyme activity. It was found that both ribozymes (CD 32 and CD 33) cleaved the RNA containing the U7 sequence (94 nucleotides long) into a 5' cleavage product with 25 nucleotides and a 3' cleavage product with 69 nucleotides. The results of these experiments are shown in FIG. 6:

Lanes m: molecular weight markers analogously to FIG. 5.

Lane 1: U7-RNA (10,000 cpm, 10 fM), incubated without ribozyme.

Lane 2: U7-RNA (10,000 cpm, 10 fM), incubated with 10 fM of the oocyte-synthesized tRNA ribozyme CD33.

Lane 3: U7-RNA (10,000 cpm, 1 pM), incubated with 10 fM of oocyte-synthesized tRNA ribozyme CD33.

Lane 4: U7-RNA (10,000 cpm, 100 fM), incubated with 10 fM of ribozyme CD32 synthesized in vitro with T7 polymerase.

Lane 5: U7-RNA (10,000 cpm, 100 fM), incubated with 1 fM of ribozyme CD32 synthesized in vitro with T7 polymerase.

EXAMPLE 4

Determining the cleaving of ribozyme substrate in oocytes.

A mixture of $^{32}$P-GTP, anti-U7-tRNA ribozyme gene and the met-tRNA gene was injected into oocyte nuclei. The injected oocytes were incubated at 20° C. for 8 hours as described in Example 2 in order to allow transcription to take place. Then radioactively labelled U7-RNA (50 nl, 100,000 cpm/µl, 100 fM/µl) was injected into the cytoplasm of the oocytes. The oocytes were then incubated for 2 hours. The preparation of the nucleic acids of individual oocytes and the separation thereof by gel electrophoresis were carried out as described above.

The results of these experiments are shown in FIG. 7:

Lanes m: molecular weight markers as in FIG. 5.

Lane 1: nucleic acids from an oocyte injected with the met and metribo genes.

Lanes 2 and 3: oocytes injected with met and metribo, followed by U7-RNA injection.

Lanes 4 and 5: oocytes injected only with U7-RNA.

Lane 6: 1 aliquot of the U7-RNA used for the injection.

Lane 7: U7-RNA (10 fM) incubated with the ribozyme CD32 (10 fM) for 2 hours at 37° C. in the presence of 150 mM NaCl, 10 mM MgCl$_2$ and 20 mM Tris-HCl, pH 7.5. Owing to the gel conditions only the 3' cleavage product (69 nucleotides) is shown.

EXAMPLE 5

Transcription activity of tRNA ribozymes in chicken cells.

Plasmid DNA molecules containing the tRNA ribozyme genes were introduced into chicken cells in order to determine the transcription activity of the genes. It was shown that the tRNA ribozyme gene (derived from a xenopus-tRNA gene) is efficiently transcribed in chicken cells. The following procedure was used: 10$^6$ primary chicken embryo fibroblast cells (Zenke et al., 1988) were seeded out in each 10 cm dish using the standard method and left to grow overnight. In the morning, each dish was transfected with 10 µg of plasmid,DNA (containing either erbB-cut 13 or ebrB-cut 53) using the calcium phosphate co-precipitation method (Graham et al., 1973). The cells were exposed to the precipitate overnight, the next morning washed twice with fresh medium and incubated for a further 48 hours in fresh medium. The medium was then removed, the cells were taken up in PK/SDS buffer (see above) and the nucleic acid was recovered. The nucleic acid was then subjected to RNAse protection mapping using $^{32}$P-labelled antisense erbB-cut 13 or erbB-cut 53 RNA probes in order to detect the presence of tRNA ribozyme transcripts. Labelled RNA (10,000 cpm/10 fM antisense-RNA per sample) were added to the dried ethanol precipitate, the sample was dried again and dissolved in 10 µl of 80% deionized formamide, 400 mM NaCl, 20 mM PIPES, pH 6,5,10 mM EDTA. The samples were coated with sterile paraffin oil, heated to 95° C. for 3 minutes and rapidly transferred into a 45° C. water bath in which they were incubated overnight. In the morning 0.3 ml of ice cold NaCl (300 mM), 30 mM of Tris, pH 7.5, 1 mM EDTA, 0.05 mg/ml of RNAS A and 80 units/ml of RNase T1, were added, with rapid careful agitation. The samples were incubated at ambient temperature for 45 minutes. Proteinase K and SDS were added to 1 mg/ml and 0.5% and incubation was continued at ambient temperature and then at 56° C., for 20 minutes in each case. The sample was precipitated with ethanol after the addition of 10 µg of tRNA. The precipitate obtained was taken up in 80% formamide/TBE and separated on a pre-heated 9.5% acrylamide/8.3 M urea/TBE gel. The results of this experiment are shown in FIG. 8:

Lanes m: molecular weight marker as in the previous examples.

Lane 1: antisense ES13 probe, hybridized with E.coli tRNA (10 Mg).

Lane 2: antisense ES53 probe, hybridized with E.coli tRNA.

Lanes 3 and 4: mapping of the nucleic acids of 10,000 and 100,000 cells which had not been transfected with plasmid DNA hybridized with the ES13 probe.

Lanes 5 and 6: mapping of the nucleic acids of 10,000 and 100,000 cells, transfected with ES13, hybridized with the ES13 probe.

Lanes 7 and 8: mapping of the nucleic acids of 10,000 and 100,000 cells, transfected with ES53, which had been hybridized with the ES13 probe.

EXAMPLE 6

Weakening of the activity of the V-erbB oncogenes by tDNA ribozyme genes which have been introduced into v-erbB transformed erythroblasts using polylysine-transferrin conjugates.

Using this example it was possible to show that tDNA ribozymes directed against the erbB oncogene are introduced into erbB-transformed chicken erythroblast by means of polylysine-transferrin-conjugates and are able to weaken the transforming activity of the oncogene.

Preliminary Test 1

Preparation of Transferrin-polylysine Conjugates

The coupling was carried out according to methods known from the literature (cf. G. Jung, W. Köhnlein and G. Lüders, Biochem. Biophys.Res. Commun. 101 (1981), 599) by the introduction of disulphide bridges after modification with succinimidylpyridyl dithiopropionate.

Pyridyldithiopropionate-modified Transferrin 1:

6 ml of a solution of 120 mg (1.5 Amol) of transferrin (from chicken albumin, Sigma, conalbumin-type I, iron-free), which had been gel-filtered over sephadex G-25, in 0.1 M sodium phosphate buffer (pH 7.8) were mixed with 200 µl of a 15 mM ethanol solution of succinimidylpyridyl dithiopropionate (SPDP, pharmacia) with thorough shaking and the mixture was left to react for 1 hour at ambient temperature with occasional shaking. Lower molecular reaction products and traces of reagent were removed by means of gel column (sephadex G-25, 14×180 mM, 0.1 M sodium phosphate buffer pH 7.8) and 7 ml of the product fraction were obtained; the content of pyridyldithiopropionate residues bound to transferrin was determined by means of one aliquot after reduction with dithiothreitol by photometric measurement of the quantity of pyridine-2-thione released and amounted to about 2.6 µmol.

Mercaptopripionate-modified Polylysine 2:

A solution of 18 mg (about 1.0 µmol) of poly(L)lysine hydrobromide (Sigma, fluoresceinisothiocyanate (=FITC)-labelled, molecular weight about 18,000—corresponding to an average degree of polymerisation of about 90) in 3 ml of 0.1 M sodium phosphate (pH 7.8) was filtered over sephadex G-25. The polylysine solution was diluted with water to 7 ml, 270 µl of a 15 mM ethanolic solution of SPDP were added with thorough shaking and the mixture was left to react for one hour in the dark at ambient temperature with occasional shaking. After the addition of 0.5 ml of 1 M sodium acetate buffer (pH 5.0, the mixture was filtered over sephadex G-25 to separate off low molecular substances (eluent: 20 mM sodium acetate buffer pH 5.0). The product fraction (stained with ninhydrin, fluorescent) was concentrated by evaporation in vacuo, adjusted to a pH of about 7 with buffer, a solution of 23 mg (150 µmol) of dithiothreitol in 200 µl of water was added and the mixture was left to stand for one hour at ambient temperature under an argon atmosphere in the dark. Excess reducing agent was removed by further gel filtration (sephadex G-25, 14×130 mM column, 10 mM sodium acetate buffer pH 5.0) and 3.5 ml of product solution of fluorescent-labelled polylysine were obtained containing 3.8 mol of mercapto groups (photometric determination) using Ellman's reagent, 5,5'-dithiobis(2-nitrobenzoic acid).

Transferrin-polylysine Conjugate 3:

The solution of modified transferrin 1 obtained as described above (7 ml in 0.1 M sodium phosphate buffer pH 7.8, about 1.5 µmol of transferrin with about 2.5 µmol of pyridyldithiopropionate residues) was rinsed with argon; 2.0 ml of the above described solution of mecapto-modified polylysine 2 (in 10 mM of sodium acetate buffer pH 5.0, corresponding to about 0.6 µmol of polylysine with about 2.2 µmol of mecapto groups) were added, the mixture was rinsed with argon, shaken and left to react for 18 hours at ambient temperature in the dark and under argon. The reaction mixture was diluted to 14 ml with water and separated by ion exchange chromatography (pharmacia mono S column HR 10/10, gradient elution, buffer A: 50 mM HEPES pH 7.9, buffer B: A+3 M sodium chloride, 0.5 ml/min). Non-conjugated transferrin was eluted first, product fractions at about 0.66–1.5 M sodium chloride. The conjugated products (ninhydrin staining, protein absorption in UV at 280 nm, and fluorescence) were collected in 6 fractions each containing about 10 mg of transferrin. First, the fractions were dialysed against a 100 mM iron (III) citrate solution (adjusted to pH 7.8 with sodium hydrogen carbonate) and then twice more against 1 mM HEPES buffer (pH 7.5). Sodium dodecyl sulphate gelelectrophoresis (10% SDS, 8% polyacrylamide) showed roughly the same content of transferrin in all six fractions when pre-treated with 2-mecaptoethanol, whereas in non-reduced samples no bands were visible for free transferrin but only for less wide ranging conjugates.

Preliminary Test 2

Transport of Transferrin-polylysine Conjugates in Living Cells

In order to show that the transferrin-polylysine conjugates described in preliminary test 1 are efficiently taken up in living erythroblasts, these conjugates were labelled with FITC. It is known (Schmidt et al., 1986) that FITC-labelled transferrin was detectable in vesicles within the cell after some hours incubation with erythroblasts from which transferrin had previously been removed (examination under a fluorescence microscope).

In the present example, erythroblasts (transformed by an EGF receptor retrovirus, Kahazaie et al., 1988) were incubated for 18 hours in transferrin-free differentiating medium (composition in Zenke et al., 1988) at 37° C. (cell concentration $1.5 \times 10^6$/ml). After the addition of the various transferrin-polylysine conjugates (or as a control, the corresponding amount of sterile twice-distilled water) the cells were incubated at 37° C. in the presence of 10 ng/ml of EGF (in order to maintain the transformed state). After 24 and 48 hours, about $5 \times 10^5$ cells were taken, washed once in phosphate-buffered physiological saline solution (PBS; pH 7.2), fixed with fifty times the volume of a mixture of 3.7% formaldehyde and 0.02% glutaraldehyde in PBS (10 min, 40° C.), washed once in PBS, embedded in Elvanol and investigated under a fluorescence microscope (Zeiss Axiophot, narrow band FITC and TRITC excitation). At the same time, the growth rate of the cells was determined in other aliquots of the various mixtures. 100 µl of cell suspension were taken and the incorporation of $^3$H-thymidine (8 µCi/ml, 2 hours) was determined, as described in Leutz et al., 1984. FIG. 10 shows that the erythroblasts incubated with transferrin-polylysine have 2 to 10 strongly fluorescing vesicles after 24 hours, which cannot be detected in the controls. Table A shows that with the exception of fraction 6 all the conjugates have been absorbed by virtually all the cells.

The fact that the cells grow equally fast in all the samples (as measured by the incorporation of tritiated thymidine ($^3$H TdR); Table A) shows that the cells are not damaged by the polylysine constructs and consequently non-specific uptake (e.g. through cell membranes which have become permeable) can be ruled out.

Preliminary Experiment 3

Polylysine-transferrin constructs can functionally replace the native transferrin-ion complex in the in vitro induced maturation of chicken erythroblasts to form erythrocytes.

The objective of this experiment was to show that the transferrin-polylysine conjugates used here can be used by the cell-like native transferrin, i.e. they can pass through the normal transferrin cycle with similar efficiency. Erythroblasts which can be induced to mature into normal erythrocytes by "switching off" the transforming oncogene are particularly suitable as a test system for this purpose (Beug et al., 1982). The literature shows that such cells require high concentrations of transferrin-iron complex for normal maturation (100–200 µg/ml, three times lower concentrations prevent the maturation of the cells and will result in the death of the cells after a few days (Kowenz et al., 1986). It has also been shown (Schmidt et al., 1986) that recycling, i.e. the reuse of transferrin receptors and hence a transferrin cycle proceeded at optimum speed is indispensable for normal in vitro differentiation.

Erythroblasts (transformed by the EGF receptor retrovirus) are induced to differentiate by the removal of EGF and addition of an optimum amount of partially purified chicken erythropoietin (Kowenz et al., 1986, free from transferring. Incubation was carried out at a cell concentration of $1 \times 10^6$/ml in transferrin-free differentiating medium at 42° C. and 5% $CO_2$. At the start of incubation, either native transferrin-iron complex (Sigma, 100 µg/ml) or the iron-saturated transferrin-polylysine conjugates (concentration again 100 µg/ml) were added. The growth and state of maturity of the cells were analyzed after 24 and 48 hours in the following way:

1. by determining the number of cells (in the Coulter Counter, Model ZM, Beug et al., 1984)
2. by recording cell size distributions (in a Coulter Channelyzer Mod. 256) and
3. by photometric measurement of the haemoglobin content of the cells (Kowenz et al., 1986)

In addition, aliquots of the mixtures were centrifuged after 72 hours in a cytocentrifuge (Shandon) on an object carrier and subject to histochemical investigation to detect the haemoglobin (staining with neutral benzidine plus Diff-Quik rapid staining for blood cells, Beug et al., 1982).

The results in Table B clearly show that cells induced to differentiate in the presence of the polylysine transferrin conjugates fractions 1 to 5 mature just as efficiently and at the same speed as those which were incubated with native transferrin-iron. The cells in the transferrin-free controls, on the hand, showed a much slower cell growth and accumulated only small quantities of haemoglobin. Investigation of the cell phenotype on stained cytospin preparations showed that the cells incubated with polylysire-transferrin conjugates were matured to produce late reticulocytes (late reticulocytes, Beug et al., 1982) in just the same way as the cells treated with native transferrin whilst the cells incubated without transferrin constituted a mixture of disintegrated and immature cells resembling erythroblasts (Schmidt et al., 1986). Only the cells treated with transferrin-polylysine fractions 6 showed a lower haemoglobin content and a higher percentage of immature cells (Table B). This shows that fractions 6, conjugated with a particularly large quantity of polylysine, functions less well in the transferrin cycle. At the same time, this result indicates the sensitivity of the test method.

Preliminary Test 4

Polylysine-transferrin conjugates permit the uptake of DNA in chicken erythroblasts.

The present experiment was intended to investigate whether DNA can be efficiently transported into the interior of the cell by transferrin-polylysine conjugates in a size corresponding to that of tDNA ribozymes (see example 1). In the present example, tDNA was used with an insert of the sequence

C G T T A A C A A G C T A A C G T T G A G G G G C A T-G A T A T C G G G C C

CCGGGCAATTGTTCGATTGCAACTCCCCGTACTATAG molecular weight about 300,000, terminally labelled with gamma $^{32}$P ATP (Maniatis). Approximately 0.3 µg of this DNA, dissolved in 20 µl of TE buffer, were mixed either with 10 µg of native transferrin, with 10 µg of transferrin-polylysine conjugate fraction 3, each of them dissolved in 50 µl of twice-distilled water, plus 400 µg/ml of bovine serum albumin (Beug et al., 1982) or with 50 µl of this solvent without transferrin. The DNA-protein mixtures were added to 2 ml of transferrin-free differentiating medium, $4 \times 10^6$ chicken erythroblasts (which had been transformed with an EGF receptor retrovirus and pre-incubated for 18 hours in transferrin-free medium in the presence of EGF (Kahazaie et al., 1988)) were added and the mixtures were incubated for 8 hours at 37° C. and 5% $CO_2$. Then the cells were removed by centrifuging, the supernatant was removed and the cells were washed three times in transferrin-free medium. The cell sediment and culture medium were taken up in 1% SDS, 1 mg/ml Proteinase K, 300 mM NaCl, 20 mM Tris pH 8.0, 10 mM EDTA (PK/SDS buffer), incubated for 30 minutes at 37° C., extracted with phenol/chloroform, and the DNA was isolated by ethanol precipitation. Isolated DNA with a radioactivity of 2000 cpm in total was separated on a non-denaturing 3.5% acrylamide gel (TBE, Maniatis) and the DNA was detected by autoradiography. The figure shows fluorescence images of chicken erythroblasts which had been incubated for 24 hours without (A) or with FITC-labelled transferrin-polylysine conjugates (B, C). When activated with blue light (B, in order to detect FITC), significantly more fluorescent vesicles can be seen in each cell. The specificity of this fluorescence is shown by the fact that the vesicle fluorescence does not occur on activation with green light (in which a non-specific fluorescence of the cells can be seen similar to that in A) (C).

This figure shows that in the cell sample treated with transferrin-polylysine, approximately five to ten times more DNA has been absorbed by the cells than in the control samples with native transferrin or with no transferrin.

Two tRNA ribozyme genes, directed against the translation initiation region of erbB were constructed (cf. FIGS. 2 and 3, Example 1). About 100 µg of each plasmid containing the gene was digested with EcoRI in order to free the tRNA ribozyme gene on a 225 bp fragment. The digestion products were terminally labelled with klenow fragment and purified by gel electrophoresis using a 2% agarose/TBE gel. The vector fragment and the tRNA ribozyme gene fragments were located by ethidiumbromide staining, cut out and obtained by electroelution, phenol/chloroform and chloroform extraction and ethanol precipitation. The purified, radioactively labelled DNA fragments were then used, making use of the transferrin-polylysine transport system, to determine the uptake and inhibition of the erbB-RNA. The vector pSPT18 was used as control-DNA.

The test cell system chosen was a chicken erythroblast cell line transformed by a temperature sensitive mutant (ts 34, Graf et al., 1978) of the avine erythroblastosis virus AEV (Beug et al, 1982 b). (The erbA oncogene which is also expressed in these cells can be inhibited by a specific protein kinase inhibitor (H7)). It has been established that the v-erbA oncogene is phosphorylated in vivo and in vitro (i.e. as a bacterially expressed protein) at two sites, namely Ser 28 and Ser 29, by protein kinase C or by cAMP-dependent protein kinase. Mutation of these serines into alanines prevents phosphorylation and destroys the v-erbA-oncogene activity. H7 is a specific inhibitor of these two kinases and is capable of selectively stopping the changes caused by v-erbA (e.g. blocking of differentiation) in erythroblasts which contain v-erbA-v-erbB.

It is known that erythroblasts in which the erbB oncogene is inactivated (e.g. by a temperature increase in the case of a temperature-sensitive erbB mutant) can be induced to cause erythrocytes to mature. One of the first indications of this process is an induction of haemoglobin synthesis which can be detected by sensitive investigation (acidic benzidine staining, Orkin et al., 1975, Graf et al., 1978) at the level of the single cell. Thus, a specific increase in the number of benzidine-positive cells could be expected as a phenotypical effect of a ribozyme directed against erbB in this test system.

The test series on which this example is based was carried out as follows: the various DNA preparations (see above and Table C), dissolved in 30 µl of TE buffer, were mixed with 10 µg of native transferrin-iron complex or transferrin-polylysine conjugate (dissolved in 50 µl of twice-distilled water) and incubated for 30 minutes at 37° C.

In the case of the vector DNA (10 µg) correspondingly more (100 µg) of transferrin preparations was used. The DNA-transferrin-DNA mixtures were each added to 1 ml of transferrin-free differentiating medium (Zenke et al., 1988). The test cells (per batch 3×10⁶) were incubated for 60 minutes at 42° C. before the test, in transferrin-free differentiating medium (to increase the uptake of transferrin) and added to the mixtures which contain DNA-transferrin. After 6 hours, 18 hours and 68 hours (for the treatment of the cells see below) samples were taken as described, separated into supernatant and cell sediment, taken up in PK/SDS buffer and the DNA was analyzed.

FIG. 9 shows that, analogously to preliminary test 4, in the cell sample treated with transferrin-polylysine, about 5–10 times more DNA was absorbed by the cells than in the control samples with native transferrin.

Trace m: molecular weight marker: pBR322 DNA, cleaved with HpaII and radioactively labelled using the Klenow fragment of DNA polymerase with alpha-$^{32}$P-CTP (Maniatis).

Trace 1: 2000 cpm ES13 fragment.

Trace 2: material from cells treated with transferrin and ES13.

Trace 3: material from cells treated with transferrin-polylysine and ES13.

After the end of incubation (6 h) the cells were centrifuged off and incubated for a further 72 hours in a transferrin-containing differentiating medium with erythropoietin and insulin (Kowenz et al., 1986, Zenke et al., 1988), 2 ml per batch, at 37° C., i.e. in the presence of an active v-erbB protein).

The following results were obtained:

1. as in preliminary test 4, an increase uptake of DNA was observed in the size of the erb-cut DNAs in the cell samples treated with transferrin-polylysine (approximately 5-fold).
2. by transfection of chicken fibroblasts with erb-cut DNA it was demonstrated that the erb-cut ribozyme tDNA is expressed in chicken cells (see example 5).
3. Table C shows that in every case where erb-cut ribozyme tDNA was introduced, with the aid of polylysine-transferrin constructs, into erbB transformed erythroblasts, the percentage of benzidine-positive cells was significantly increased (approximately doubled) the reference used was the samples treated with vector DNA, in which the use of polylysine-transferrin conjugates, as expected, did not result in an increase in the number of benzidine-positive cells).

EXAMPLE 7

Extending the anticodon stem region increases the yield of ribtRNA.

The human met tRNA gene (cloned as a bamHI/RsaI fragment, complemented by EcoRI linker in the EcoRI cutting site of the Bluescript vector) was cleaved at its single ApaI cutting site in the anticodon stem region. The single-strand overhangs were removed by treatment with T4-DNA polymerase and oligonucleotides containing the ribozyme sequences were inserted. The ribozyme insertion used in the preceding examples resulted in a ribtRNA molecule containing a three-base stem (FIG. 11 shows the wild-type tRNA met and the tRNA rib with the shortened anticodon stem). In the second construction an oligonucleotide was used which differs from the first by the sequence GGTTAT, complimentary to the wild-type sequence, at the 5' end. The wild-type strain was reestablished and extended by four additional base pairs (FIG. 12 shows the construction of the tRNA rib with the strengthened anticodon stem. The sequence of the ribozymes is shown in FIG. 13; at the left hand (5') end are shown the differences in the nucleotide sequences between the region coding for the shortened stem and the region coding for the strengthened stem. FIG. 13 also shows the sequence of the met tRNA gene). The two ligation products were transformed in E.coli HB 101 using the standard method described in Maniatis, the plasmid DNA was isolated and sequenced in order to determine the correct structure. The two resulting ribtRNA genes were investigated by microinjection of the cloned DNA into xenopus oocytes, carried out as described in Example 2 or 3, in the presence of $32_P$-GTP, for any evidence of transcription activity and accumulation of the ribtRNA molecules. The wild-type tRNA gene was co-injected at a ten times lower concentration. The injected oocytes were incubated for 7 hours at 20° C. and the resulting RNA was harvested (cf. Example 2) and separated by electrophoresis (10% acrylamide/8.3 M urea/TBE gel) and the RNA molecules were made visible by autoradiography (two days exposure at −70° C.) (FIG. 14). The shortened ribtRNA gene yields about one tenth of the quantity of RNA transcribed by the wild-type gene, whilst in contrast the gene which codes for the ribtRNA molecule with the longer stem yields six times as much RNA.

EXAMPLE 8

Expression of ribozyme genes as a constituent of introns.

The starting gene used was a Xenopus Laevis tRNA$^{tyr}$C gene (oocyte-type) containing an intron comprising 13 nucleotides. The natural intron sequence was modified as follows: first of all, a suitable restriction cutting site was inserted (ApaI; GGGCCC), to permit subsequent cloning of oligonucleotides, and secondly complimentary nucleotides to the anticodon triplet were inserted in order to have an additionally stabilising structural feature by extending the intron sequence. The size of the intron in the modified gene is increased from 13 to 15 nucleotides (FIG. 15).

The modification of the intron sequence was carried out using the polymerase chain reaction (PCR; Ho et al., 1989). Four primers were synthesized, two of which contain the altered intron sequence (complimentary to one another) whilst two were directed against the 5' or 3' end, respectively, of the gene, in order to introduce an EcoRI or SalI restriction cutting site. The wild-type gene was present as an HhaI fragment(258 bp), cloned in pBR327 (Stutz et al., 1989). The resulting PCR product was purified over an agarose gel, cut with the abovementioned restriction enzymes and ligated with the vector pAALM (=pSP64+T7 promoter; Vieira and Messing, 1982). The construct was transformed in E.coli HB 101 and clones containing the desired insert were identified by sequence analysis.

The activity of the modified gene (tRNA$^{tyr}$M), was compared with that of the wild-type gene by microinjection into xenopus oocytes, whilst an as an internal standard a 5S-RNA gene (fifty times lower concentration), which was present on the plasmid pUC-10-5S (Carroll and Brown, 1976), was co-injected in the presence of $32_P$GTP. The injected oocytes were incubated for 20 hours at 20° C., the RNA was separated on an 8% acrylamide/8.3 M urea/TBE gel and autoradiographed (FIG. 16). In addition to the 5S-RNA at 120 nt the primary tRNA$^{tyr}$ transcript was visible at 100 (102) nt, the 5' and 3' processed precursor form at 90 (92) nt and the finished processed tyrosine tRNA at 76 nt. The splicing of the 90 nt precursor form appears to be the limiting factor, with the result that the majority of the transcript formed (about 80%) is present in this form. As expected, the biological activity was not reduced by a modification from the wild-type gene.

In another experiment the capacity of the system was tested. Two oligodeoxyribonucleotides which contained ribozyme sequences were synthesized, which already contain ApaI ends and were thus able to be cloned directly into the intron sequence of the modified tRNA$^{tyr}$ gene. In an oligonucleotide, 12 nt were inserted at both ends in order to form stable "hairpins" in ribintrons and thus counteract the degradation of exonuclease. The overall size of the resulting introns was 80 nt (ribozyme HP) as compared to 65 nt in the case of the unprotected ribozyme sequence (ribozyme C). the sequences of the ribozymes and the cloning plan are shown in FIG. 17.

For the microinjections into xenopus oocytes, analogous with those described above, in addition to the two constructs already described a third was used which contains the ribozyme HP in dimeric form and thus increases the intron size to 163 nt (ribozyme D). The concentration of the co-injected 5S standard was 1:20 for constructs HP and D and 1:1 for construct C (FIG. 18). The experiment shows, that, in spite of substantially enlarged introns, the constructs HP and C are very actively transcribed and processed with the same efficiency as the wild-type tRNA$^{tyr}$ gene. In the case of construct D, only a minimal quantity of transcript is detectable since obviously the secondary structure required for the formation of a PoI III transcription complex was destroyed by the long intron sequence.

It was possible to demonstrate that the expression of ribozymes as introns of tRNAs does not result in any major deterioration in the tRNA secondary structure, as a result of which the transcript produced can be accumulated in a high concentration and processed correctly.

Bibliography:

Altmann et al. (1988), Structure and Function of Major and Minor Small Nuclear Ribonucleoprotein Particles, Herausgeber Birnstiel, Springer Verlag, Berlin, 183–195
Beug et al. (1982a), J.Cell Physiol. Suppl.1, 195–207
Beug et al. (1982b), Cell 28, 907–919
Beug et al. (1984), Cell 36, 963–972
Caroll and Brown, (1976), Cell 7, 477–486
Ciliberto et al. (1982), Proc.Natl.Acad.Sci.79, 1921–1925
Clarkson, Eukaryotic Genes, Their Structure, Activity and Regulation, Herausgeber: McLean et al., Butterworth (1983), 239–261
Cotten et al. (1988), EMBO J., 7, 801–808
Felgner et al. (1987), Proc.Natl.Acad.Sci. 84, 7413–7417
Folk et al. (1983), Cell 33, 585–593
Fromm et al. (1987), Methods in Enzymol. 153, 351–366
Geiduschek et al. (1988), Ann.Rev.Biochem. 57, 873–914
Gref et al. (1978), Nature 275, 496–501
Graham et al. (1973), Virology 52, 456–467
Hampel u.Tritz (1989), Biochemistry 28, 4929–4933
Haseloff et al. (1988), Nature 334, 585–591
Ho et al. (1989), Gene 77, 51–59
Hofstetter et al. (1981), Cell 24, 573–585
Jennings et al. (1987), EMBO J. Vol.6, 10, 3043–3047
Jung et al. (1981), Biochem.Res.Commun.101, 599
Kahazaie et al. (1998), EMBO J. 10, 3061–3071
Kowenz et al (1986), Mod.Trends in Human Leukemia VII, Springer Verlag, 199–209
Kressmann et al. (1978), Proc.Natl.Acad.Sci. 75, 1176–1180
Kressmann et al. (1980), Series 31, 383–407
Kuo et al. (1988), J.Virol. 4439–4444
Langridge et al. (1987), Methods Enzymol. 153, 336–351
Leutz et al. (1984), EMBO J. 3, 3191–3197
Maniatis et al. (1982), Molecular Cloning, Cold Spring Harbor
Melton et al. (1984), Nucleic Acids Res. 12, 7035–7056
Mowry et al. (1987), Science 238, 1682–1687
Orkin et al. (1975), Proc.Natl.Acad.Sci. 72, 98–102
Pepperkok et al. (1988), Proc.Natl.Acad.Sci.85, 6748–6752
Schmidt et al. (1986), Cell 46, 41–51
Sharmeen et al. (1988), J.Virol.62, 2674–2679
Soldati et al. (1988), Mol.Cell.Biol.8, 1518–1524
Stewart et al. (1987), EMBO J.6, 383–388
Stutz et al. (1989), Genes & Development Vol.3, 8, 1190–1198
Tellford et al. (1979), Proc.Acad.Sci. 76, 2590–2594
Uhlenbeck et al. (1987), Nature 328, 596–600
Vennstrom et al. (1980), J.Virol. 36, 575–585
Viera und Messing, (1982), Gene 19, 259–268
Wu et al. (1989), Proc.Natl.Acad.Sci. 86, 1831–1835
Zasloff et al. (1982), Nature 300, 81–84
Zasloff et al. (1983), Proc.Acad.Sci. 80, 6426–6440
Zenke et al. (1988), Cell 52, 107–119

TABLE A

Transporting of Polylysin-transferrin into erythroblasts

| Batch | Medium | Transferrin-polyLysin | Vesicle fluorescence 24 h | Vesicle fluorescence 48 h | Viability (3H Td R-incorporation) 48 h |
|---|---|---|---|---|---|
| 1 | 2 ml | without addition | <1% | <1% | 140.000 cpm |
| 2 | 2 ml | 145 µl H$_2$O | <1% | <1% | 126.000 cpm |
| 3 | 2 ml | 145 µl TfpL Fr1 | >90%++ | >90%++ | 137.000 cpm |
| 4 | 2 ml | 145 µl TfpL Fr2 | >90%+++ | >90%+++ | 161.000 cpm |
| 5 | 2 ml | 145 µl TfpL Fr3 | >90%+++ | >90%+++ | 153.000 cpm |
| 6 | 2 ml | 145 µl TfpL Fr4 | ca. 80%+++ | >90%+++ | 151.000 cpm |

TABLE A-continued

Transporting of Polylysin-transferrin into erythroblasts

| Batch | Medium | Transferrin-polyLysin | Vesicle fluorescence 24 h | | Viability (3H Td R-incorporation) 48 h |
|---|---|---|---|---|---|
| | | | 24 h | 48 h | 48 h |
| 7 | 2 ml | 145 µl TfpL Fr5 | ca. 60%+++ | >90%+++ | 153.000 cpm |
| 8 | 2 ml | 145 µl TfpL Fr6 | ca. 40%+++ | >90%+++ | 165.000 cpm |

++ and +++ indicate the relative intensity of the vesicle fluorescence

TABLE B

PolyLysin-Transferrin can functionally replace normal Transferrin in the stimulation of the in vitro-induced maturation of erythroblasts

| No | Medium | Addition[b] | No of cells (× 10⁶/ml) | | Hemoglobin E 492 | | Degree of maturity % reticulocytes |
|---|---|---|---|---|---|---|---|
| | | | 24 h | 48 h | 24 h | 48 h | 72 h |
| 1 | 2 ml | Fe-Transferrin | 3.28 | 4.38 | 1.38 | 2.74 | >80% |
| 2 | 2 ml | — | 2.62 | 2.56 | 0.35 | 0.23 | <1% |
| 3 | 2 ml | H₂O | 2.60 | 2.42 | 0.30 | 0.13 | <1% |
| 4 | 2 ml | TfpL Fr1 | 3.70 | 4.44 | 1.36 | 2.69 | >80% |
| 5 | 2 ml | TfpL Fr2 | 3.56 | 4.24 | 1.16 | 2.51 | n.b.[a] |
| 6 | 2 ml | TfpL Fr3 | 3.72 | 4.54 | 1.58 | 2.54 | >80% |
| 7 | 2 ml | TfpL Fr4 | 3.48 | 4.56 | 1.57 | 2.55 | n.b. |
| 8 | 2 ml | TfpL Fr5 | 3.36 | 4.26 | 1.41 | 2.47 | n.b. |
| 9 | 2 ml | TfpL Fr6 | 3.58 | 4.4 | 1.14 | 1.93 | 60–65% |

[a]not determined
[b]Fe-Transferrin, 200 µg in 13 µl; TfpL-fraction 200 µg in 130 µl; H₂O, 130 µl

TABLE C

Maturation (hemoglobin content) of v-erbB - transformed erythroblasts which have absorbed v-erbB - ribozyme DNA

| | DNA | | | Transferrin | | Hemoglobin content (% positive of the acetic benzidine staining) | |
|---|---|---|---|---|---|---|---|
| No | Type | MW | Amount | Type | Amount | 14 h | 62 h |
| 1 | erb-cut | 13 | 2 × 10⁵ 1 µg | Tf | 10 µg | <1 | 15 +− 3[a] (3)[b] |
| 2 | erb-cut | 13 | | TfpL Fr5 | 10 µg | <1 | 37 +− 4 (2) |
| 3 | erb-cut | 53 | 2 × 10⁵ 1 µg | Tf | 10 µg | <1 | 25 +− 2 (2) |
| 4 | erb-cut | 53 | | TfpL Fr5 | 10 µg | <1 | 42 +− 1 (2) |
| 5 | Vector without ribozyme | | 2 × 10⁶ 10 µg | Tf | 100 µg | <1 | 23 +− 3 (2) |
| 6 | Vector without ribozyme | | 10 µg | TfpL Fr5 | 100 µg | <1 | 22 +− 2 (2) |
| 7 | erb-cut | 13 +53 | s.o. 0.5 +0.5 µg | Tf | 10 µg | <1 | 21 +− 2 (2) |
| 8 | erb-cut | 13 +53 | 0.5 +0.5 µg | TfpL Fr5 | 10 µg | <1 | 38 +− 2 (2) |

[a]more than 200 cells were counted out for each measurement values +or − standard deviation
[b]No. of independent measurements

What is claimed is:

1. A polynucleotide molecule, comprising:
   (a) a first polynucleotide molecule coding for a tRNA; and
   (b) a second polynucleotide molecule coding for a ribozyme, said second polynucleotide molecule being located between the A- and B-boxes of said first polynucleotide molecule.

2. The polynucleotide molecule of claim 1, wherein said first polynucleotide molecule comprises an ApaI restriction site located between said A and B boxes, and said second polynucleotide molecule is inserted in said ApaI restriction site.

3. The polynucleotide molecule of claim 1, wherein said ribozyme is a hammerhead-type ribozyme.

4. The polynucleotide molecule of claim 1, wherein said first polynucleotide molecule codes for initiation-met tRNA.

5. The polynucleotide molecule of claim 1, wherein said first polynucleotide molecule codes for tyr-tRNA.

6. The polynucleotide molecule of claim 1, further comprising an intron, wherein said intron is part of said second polynucleotide molecule.

7. The polynucleotide molecule of claim 6, wherein said intron is modified by first insertion of a restriction site and a second insertion of nucleotides complimentary to the anticodon triplet, so that the secondary structure of the precursor tRNA is stabilized, while the structures which are critical for splicing are maintained.

8. The polynucleotide molecule of claim 1, wherein said first polynucleotide molecule codes for a tRNA having an anticodon stem and loop region, and wherein said anticodon stem and loop region is longer than the anticodon stem and loop region of the wild-type tRNA.

9. The polynucleotide molecule of claim 8, further comprising a restriction site introduced into the anticodon stem and loop region, and wherein said second polynucleotide molecule is inserted in said restriction site.

10. A polynucleotide molecule, comprising:
   (a) a first polynucleotide molecule coding for a tRNA;
   (b) a second polynucleotide molecule coding for a ribozyme, said second polynucleotide molecule being located between the A- and B-boxes of said first polynucleotide molecule; and (c) an intron that is part of said second polynucleotide molecule.

11. The polynucleotide molecule of claim 10, wherein said intron is modified by a first insertion of a restriction site and a second insertion of nucleotide complimentary to the anticodon triplet, so that the secondary structure of the precursor tRNA is stabilized, while the structures which are critical for splicing are maintained.

12. A polynucleotide molecule, comprising:
(a) a first polynucleotide molecule coding for a tRNA having an anticodon stem and loop region, wherein said anticodon stem and loop region is longer than the anticodon stem and loop region of the wild-type tRNA; and
(b) a second polynucleotide molecule coding for a ribozyme, said second polynucleotide molecule being located between the A- and B-boxes of said first polynucleotide molecule.

13. A polynucleotide molecule, comprising:
(a) a first polynucleotide molecule that is transcribed by RNA polymerase III; and
(b) a second polynucleotide molecule coding for an RNA-inhibiting RNA located within said first polynucleotide molecule, wherein said RNA-inhibiting RNA is not an antisense molecule.

14. The polynucleotide molecule of claim 13, wherein said first polynucleotide molecule codes for a tRNA.

15. The polynucleotide molecule of claim 14, wherein said first polynucleotide molecule codes for initiation-met tRNA.

16. The polynucleotide molecule of claim 14, wherein said first polynucleotide molecule codes for tyr-tRNA.

17. The polynucleotide molecule of claim 14, further comprising an intron, wherein said intron is part of said second polynucleotide molecule.

18. The polynucleotide molecule of claim 14, wherein said first polynucleotide molecule codes for a tRNA having an anticodon stem and loop region, and wherein said anticodon stem and loop region is longer than the anticodon stem and loop region of the wild-type tRNA.

19. The polynucleotide molecule of claim 18, further comprising a restriction site introduced into the anticodon stem and loop region, and wherein said second polynucleotide molecule is inserted in said restriction site.

20. A nucleic acid molecule, comprising:
(a) a first polynucleotide molecule that is transcribed by RNA polymerase III; and
(b) a second polynucleotide molecule coding for an RNA-inhibiting RNA that is not an antisense molecule, wherein said second polynucleotide molecule is inserted within said first polynucleotide molecule in such a way that, when said nucleic acid molecule is transcribed by RNA polymerase III, the transcription rate of said nucleic acid molecule and the stability of the resulting transcript are maintained.

21. The nucleic acid molecule of claim 20, wherein said RNA-inhibiting RNA is a ribozyme.

22. The nucleic acid molecule of claim 20, wherein said first polynucleotide molecule codes for a tRNA.

23. The nucleic acid molecule of claim 20, wherein said first polynucleotide molecule codes for initiation-met tRNA.

24. The nucleic acid molecule of claim 20, wherein said first polynucleotide molecule codes for tyr-tRNA.

25. The nucleic acid molecule of claim 20, further comprising an intron, wherein said intron is part of said second polynucleotide molecule.

26. The nucleic acid molecule of claim 20, wherein said first polynucleotide molecule codes for a tRNA having an anticodon stem and loop region, and wherein said anticodon stem and loop region is longer than the anticodon stem and loop region of the wild-type tRNA.

27. The nucleic acid molecule of claim 26, further comprising a restriction site introduced into the anticodon stem and loop region, and wherein said second polynucleotide molecule is inserted in said restriction site.

* * * * *